United States Patent
Menet et al.

(10) Patent No.: US 8,088,764 B2
(45) Date of Patent: Jan. 3, 2012

(54) COMPOUND USEFUL FOR THE TREATMENT OF DEGENERATIVE AND INFLAMMATORY DISEASES

(75) Inventors: Christel Jeanne Marie Menet, Mechelen (BE); Koen Kurt Smits, Mechelen (BE)

(73) Assignee: Galapagos NV, Mechelen (BE)

( * ) Notice: Subject to any disclaimer, the term of this patent is extended or adjusted under 35 U.S.C. 154(b) by 0 days.

(21) Appl. No.: 12/823,654

(22) Filed: Jun. 25, 2010

(65) Prior Publication Data

US 2010/0331319 A1 Dec. 30, 2010

Related U.S. Application Data

(60) Provisional application No. 61/220,688, filed on Jun. 26, 2009.

(51) Int. Cl.
*A61K 31/541* (2006.01)
*C07D 487/04* (2006.01)

(52) U.S. Cl. .................................... 514/228.5; 544/58.2

(58) Field of Classification Search .................. 544/58.2; 514/228.5

See application file for complete search history.

(56) References Cited

FOREIGN PATENT DOCUMENTS

| WO | WO 03/010167 A1 | 2/2003 |
|---|---|---|
| WO | WO 2005/124342 A2 | 12/2005 |
| WO | WO 2009/017954 A1 | 2/2009 |
| WO | WO 2009/047514 A1 | 4/2009 |
| WO | WO 2009/155565 A1 | 12/2009 |
| WO | WO 2010/010189 A1 | 1/2010 |
| WO | WO 2010/010190 A1 | 1/2010 |
| WO | WO 2010/141796 A2 | 12/2010 |

OTHER PUBLICATIONS

O'Sullivan, L.A., et al., "Cytokine receptor signaling through the Jak-Stat-Socs pathway in disease," 2007 Molecular Immunology 44 (2007) 2497-2506.
Oste L., et al., ECTC Montreal 2007: "A High Throughout Method of Measuring Bone Achitectural Disturbance in a Murine CIA Model by Micro-CT Morphometry." (Flyer).
Oste L., et al., ECTC Montreal 2007: "A High Throughout Method of Measuring Bone Achitectural Disturbance in a Murine CIA Model by Micro-CT Morphometry."
Nettekoven, M., et al., "Synthetic Access to 2-Amido-5-aryl-8-methoxy-triazolopyridine and 2-Amido-5-morpholino-8-methoxy-triazolopyridine Derivatives as Potential Inhibitors of the Adenosine Receptor Subtypes," Snythesis 2003, No. 11, (2003) 1649.
McGinnity, Dermot F., et al., "Evaluation of Fresh and Cryopreserved Hepatocytes as in Vitro Drug Metabolism Tools for the Prediction of Metabolic Clearance," Drug Metabolism and Disposition, 32:1247-1253, 2004.
Wernig et al. (2008) Efficacy of TG101348, a selective JAK2 inhibitor, in treatment of a murine model of JAK2V617F-induced polycythemia vera, Cancer Cell 13(4), 311-320.
Geron et al. (2008) Selective inhibition of JAK2-driven erythroid differentiation of polycythemia vera progenitors Cancer Cell 13 (4), 321-30.
Wirtz et al. (2007) Mouse Models of Inflammatory Bowel Disease, Advanced Drug Delivery Reviews, 2007, 1073-1083.
Nials et al. (2008) Mouse Models of Allergic Asthma: Acute and Chronic Allergen Challenge, Disease Models & Mechanisms, 213-220.
Ip et al. (2006) Interleukin (IL)-4 and IL-13 up-regulate monocyte chemoattractant protein-1 expression in human bronchial epithelial cells: involvement of p38 mitogen-activated protein kinase, extracellular signal-regulated kinase 1/2 and Janus kinase-2 but not c-Jun NH2-terminal kinase 1/ 2 signalling pathways, Clin. Exp. Immun, 162-172.
Pernis et al. (2002) JAK-STAT signaling in asthma J. Clin. Invest. 1279.
Kudlacz et al. (2008) The JAK-3 inhibitor CP-690550 is a potent anti-inflammatory agent in a murine model of pulmonary eosinophilia, Eur J Pharmaco 154-161.
Mullighan CG, Zhang J, Harvey RC, Collins-Underwood JR, Schulman BA, Phillips LA, Tasian SK, Loh ML, Su X, Liu W, Devidas M, Atlas SR, Chen I-M, Clifford RJ, Gerhard DS, Carroll WL, Reaman GH, Smith M, Downing JR, Hunger SP Willmane CL; (2009) JAK mutations in high-risk childhood acute lymphoblastic leukemia, PNAS May 22. [E pub ahead of print].
Argiles JM, Lopez-Soriano FJ. (1998)Catabolic proinflammatory cytokines. Curr Opin Clin Nutr Metab Care. 1:245-51.

(Continued)

Primary Examiner — Kahsay T Habte
(74) Attorney, Agent, or Firm — Klauber & Jackson LLC

(57) ABSTRACT

A novel compound able to inhibit JAK is disclosed, that comprises a compound according to Formula I:

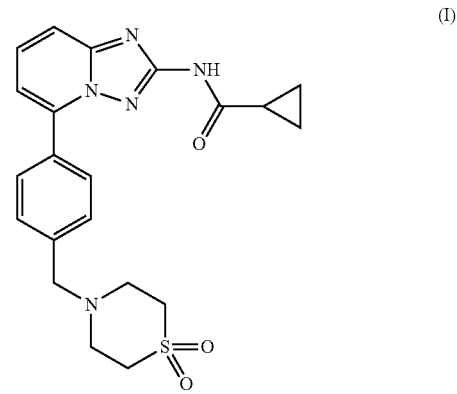

or a pharmaceutically acceptable salt thereof. The compound may be prepared as a pharmaceutical composition, and may be used for the treatment of a variety of conditions in mammals including humans, including by way of non-limiting example, inflammatory conditions, autoimmune diseases, proliferative diseases, transplantation rejection, diseases involving impairment of cartilage turnover, congenital cartilage malformations, and/or diseases associated with hypersecretion of IL6.

15 Claims, No Drawings

OTHER PUBLICATIONS

Bush KA, Farmer KM, Walker JS, Kirkham BW. (2002) Reduction of joint inflammation and bone erosion in rat adjuvant arthritis by treatment with interleukin-17 receptor IgG1 Fc fusion protein. Arthritis Rheum. 46: 802-5.

Jou IM, Shiau AL, Chen SY, Wang CR, Shieh DB, Tsai CS, Wu CL. (2005) Thrombospondin 1 as an effective gene therapeutic strategy in collagen-induced arthritis. Arthritis Rheum. 52:339-44.

Nishida K, Komiyama T, Miyazawa S, Shen ZN, Furumatsu T, Doi H, Yoshida A, Yamana J, Yamamura M, Ninomiya Y, Inoue H, Asahara H. (2004) Histone deacetylase inhibitor suppression of autoantibody-mediated arthritis in mice via regulation of p16INK4a and p21(WAF1/Cip1) expression. Arthritis Rheum. 10: 3365-76.

Rall LC, Roubenoff R.(2004) Rheumatoid cachexia: metabolic abnormalities, mechanisms and interventions. Rheumatology; 10:1219-23.

Salvemini D, Mazzon E, Dugo L, Serraino I, De Sarro A, Caputi AP, Cuzzocrea S. (2001) Amelioration of joint disease in a rat model of collagen-induced arthritis by M40403, a superoxide dismutase mimetic. Arthritis Rheum. 44:2909-21.

Shelton DL, Zeller J, Ho WH, Pons J, Rosenthal A. (2005) Nerve growth factor mediates hyperalgesia and cachexia in auto-immune arthritis. Pain. 116:8-16.

Sims NA, Green JR, Glatt M, Schlict S, Martin TJ, Gillespie MT, Romas E. (2004) Targeting osteoclasts with zoledronic acid prevents bone destruction in collagen-induced arthritis. Arthritis Rheum., 50: 2338-46.

Walsmith J, Abad L, Kehayias J, Roubenoff R. (2004) Tumor necrosis factor-alpha production is associated with less body cell mass in women with rheumatoid arthritis. J Rheumatol.; 31:23-9.

Khachigian, L. M. Collagen antibody-induced arthritis. (2006) Nature Protocols 1, 2512-6.

Lin HS, Hu CY, Chan HY, Liew YY, Huang HP, Lepescheux L, Bastianelli E, Baron R, Rawadi G, Clément-Lacroix P. (2007) Anti-rheumatic activities of histone deacetylase (HDAC) inhibitors in vivo in collagen-induced arthritis in rodents. Br J Pharmacol. Apr;150 (7):829-31.

Xiang, S, et al., "Identification of somatic JAK1 mutations in patients with acute myeloid leukemia," 2008 Blood, 111:4809-4812.

Choy EH, Panayi GS. (2001). N Engl J Med. 344: 907-16.

Chubinskaya S and Kuettner KE (2003). Regulation of osteogenic proteins by chondrocytes. The international journal of biochemistry & cell biology 35(9)1323-1340.

Clegg DO et al. (2006) N Engl J Med. 2006 354:795-808. Glucosamine, chondroitin sulfate, and the two in combination for painful knee osteoarthritis.

Firestein GS. (2003). Nature. 423:356-61.

Lee DM, Weinblatt ME (2001). Lancet. 358: 903-11.

Legendre F, Dudhia J, Pujol J-P, Bogdanowicz P. (2003) JAK/STAT but not ERK1/ERK2 pathway mediates interleuking (IL)-6/soluble IL-6R down-regulation of type II collagen, aggrecan core, and link protein transcription in articular chondrocytes. J. Biol. Chem. 278(5)2903-2912.

Li WQ, Dehnade F, Zafarullah M. (2001) Oncostatin M-induced matrix metalloproteinase and tissue inhibitor of metalloproteinase-3 genes expression in chondrocytes requires janus kinase/STAT signaling pathway. (2001) J. Immunol. 166:3491-3498.

O'Dell JR. (2004) Therapeutic strategies for rheumatoid arthritis. N Engl J Med. 350(25):2591-602.

Osaki M, Tan L, Choy BK, Yoshida Y, Cheah KSE, Auron PE, Goldring MB. (2003) The TATA-conatining core promoter of the type II collagen gene (COL2A1) is the target of interferon-gamma-mediated inhibition in human chondrocytes: requirement for STAT1ALPHA, JAK1 and JAK2. Biochem J 369:103-115.

Otero M, Lago R, Lago F, Gomez Reino JJ, Gualillo O. (2005) Signalling pathway involved in nitric oxide synthase type II activation in chondrocytes: synergistic effect of leptin with interleukin-1. Arthritis Research & therapy 7: R581-R591.

Sims NA et al., (2004) Targeting osteoclasts with zoledronic acid prevents bone destruction in collagen-induced arthritis, Arthritis Rheum. 50 2338-2346.

Rodig SJ, Meraz MA, White JM, Lampe PA, Riley JK, Arthur CD, King KL, Sheehan KCF, Yin L, Pennica D, Johnson EM, Schreiber RD. (1998) Disruption of the Jak1 gene demonstrates obligatory and nonredundant roles of the jaks in cytokine-induced biologic responses Cell 93: 373-383.

Smolen JS, Steiner G. (2003). Nat Rev Drug Discov. 2: 473-88.

Wieland HA, Michaelis M, Kirschbaum BJ, Rudolphi KA. (2005). Nat Rev Drug Discov. 4:331-44. Osteoarthritis—an untreatable disease?

Tam, L., McGlynn, L.M., Traynor, P., Mukherjee, R., Bartlett, J.M.S., Edwards, J. (2007) British Journal of Cancer, 97, 378-383.

Constantinescu et al., 2007, Trends in Biochemical Sciences 33(3): 122-131.

Tetsuji Naka, Norihiro Nishimoto and Tadamitsu Kishimoto, Arthritis Res 2002, 4 (suppl 3):S233-S242.

O'Shea J. et al. Nature Review Drug Discovery 3 (2004) 555-564: A new modality for immunesuppresion: targeting the JAK/STAT pathway.

Vainchenker W. et al. Seminars in Cell & Developmental Biology 19 (2008) 385-393: JAKs in pathology: Role of Janus kinases in hematopoietic malignancies and immune deficiencies.

Levy D. and Loomis C. New England Journal of Medicine 357 (2007) 1655-1658: STAT3 signaling and the Hyper-IgE-syndrome.

US 8,088,764 B2

COMPOUND USEFUL FOR THE TREATMENT OF DEGENERATIVE AND INFLAMMATORY DISEASES

RELATED APPLICATIONS

The present application claims the benefit under 35 U.S.C. §119 of U.S. Provisional Application No. 61/220,688, filed Jun. 26, 2009, the contents of which is hereby incorporated herein by reference in its entirety.

FIELD OF THE INVENTION

The present invention relates to a compound that is an inhibitor of JAK, a family of tyrosine kinases that are involved in inflammatory conditions, autoimmune diseases, proliferative diseases, transplantation rejection, diseases involving impairment of cartilage turnover, congenital cartilage malformations, and/or diseases associated with hypersecretion of IL6. In particular, the compound of the invention inhibits JAK1 and JAK2. The present invention also provides methods for the production of the compound of the invention, pharmaceutical compositions comprising the compound of the invention, methods for the prevention and/or treatment of diseases involving inflammatory conditions, autoimmune diseases, proliferative diseases, transplantation rejection, diseases involving impairment of cartilage turnover, congenital cartilage malformations, and/or diseases associated with hypersecretion of IL6 by administering the compound of the invention.

Janus kinases (JAKs) are cytoplasmic tyrosine kinases that transduce cytokine signaling from membrane receptors to STAT transcription factors. Four JAK family members are described, JAK1, JAK2, JAK3 and TYK2. Upon binding of the cytokine to its receptor, JAK family members auto- and/or transphosphorylate each other, followed by phosphorylation of STATs that then migrate to the nucleus to modulate transcription. JAK-STAT intracellular signal transduction serves the interferons, most interleukins, as well as a variety of cytokines and endocrine factors such as EPO, TPO, GH, OSM, LIF, CNTF, GM-CSF and PRL (Vainchenker W. et al. (2008)).

The combination of genetic models and small molecule JAK inhibitor research revealed the therapeutic potential of several JAKs. JAK3 is validated by mouse and human genetics as an immune-suppression target (O'Shea J. et al. (2004)). JAK3 inhibitors were successfully taken into clinical development, initially for organ transplant rejection but later also in other immuno-inflammatory indications such as rheumathoid arthritis (RA), psoriasis and Crohn's disease (http://clinicaltrials.gov/).

TYK2 is a potential target for immuno-inflammatory diseases, being validated by human genetics and mouse knockout studies (Levy D. and Loomis C. (2007)).

JAK1 is a novel target in the immuno-inflammatory disease area. JAK1 heterodimerizes with the other JAKs to transduce cytokine-driven pro-inflammatory signaling. Therefore, inhibition of JAK1 and/or other JAKs is expected to be of therapeutic benefit for a range of inflammatory conditions as well as for other diseases driven by JAK-mediated signal transduction.

BACKGROUND OF THE INVENTION

The degeneration of cartilage is the hallmark of various diseases, among which rheumatoid arthritis and osteoarthritis are the most prominent. Rheumatoid arthritis (RA) is a chronic joint degenerative disease, characterized by inflammation and destruction of the joint structures. When the disease is unchecked, it leads to substantial disability and pain due to loss of joint functionality and even premature death. The aim of an RA therapy, therefore, is not only to slow down the disease but to attain remission in order to stop the joint destruction. Besides the severity of the disease outcome, the high prevalence of RA (~0.8% of the adults are affected worldwide) means a high socio-economic impact. (For reviews on RA, we refer to Smolen and Steiner (2003); Lee and Weinblatt (2001); Choy and Panayi (2001); O'Dell (2004) and Firestein (2003)).

Osteoarthritis (also referred to as OA, or wear-and-tear arthritis) is the most common form of arthritis and is characterized by loss of articular cartilage, often associated with hypertrophy of the bone and pain. For an extensive review on osteoarthritis, we refer to Wieland et al. (2005).

Osteoarthritis is difficult to treat. At present, no cure is available and treatment focuses on relieving pain and preventing the affected joint from becoming deformed. Common treatments include the use of non-steroidal anti-inflammatory drugs (NSAIDs). Although dietary supplements such as chondroitin and glucosamine sulphate have been advocated as safe and effective options for the treatment of osteoarthritis, a recent clinical trial revealed that both treatments did not reduce pain associated to osteoarthritis. (Clegg et al., 2006).

Stimulation of the anabolic processes, blocking catabolic processes, or a combination of these two, may result in stabilization of the cartilage, and perhaps even reversion of the damage, and therefore prevent further progression of the disease. Therapeutic methods for the correction of the articular cartilage lesions that appear during the osteoarthritic disease have been developed, but so far none of them have been able to mediate the regeneration of articular cartilage in situ and in vivo. Taken together, no disease modifying osteoarthritic drugs are available.

Vandeghinste et al. (WO 2005/124342) discovered JAK1 as a target whose inhibition might have therapeutic relevance for several diseases including OA. Knockout of the JAK1 gene in mice demonstrated that JAK1 plays essential and non-redundant roles during development: JAK1−/− mice died within 24 h after birth and lymphocyte development was severely impaired. Moreover, JAK1−/− cells were not, or less, reactive to cytokines that use class II cytokine receptors, cytokine receptors that use the gamma-c subunit for signaling and the family of cytokine receptors that use the gp130 subunit for signaling (Rodig et al., 1998).

Various groups have implicated JAK-STAT signaling in chondrocyte biology. Li et al. (2001) showed that Oncostatin M induces MMP and TIMP3 gene expression in primary chondrocytes by activation of JAK/STAT and MAPK signaling pathways. Osaki et al. (2003) showed that interferon-gamma mediated inhibition of collagen II in chondrocytes involves JAK-STAT signaling. IL1-beta induces cartilage catabolism by reducing the expression of matrix components, and by inducing the expression of collagenases and inducible nitric oxide synthase (NOS2), which mediates the production of nitric oxide (NO). Otero et al., (2005) showed that leptin and IL1-beta synergistically induced NO production or expression of NOS2 mRNA in chondrocytes, and that that was blocked by a JAK inhibitor. Legendre et al. (2003) showed that IL6/IL6Receptor induced downregulation of cartilage-specific matrix genes collagen II, aggrecan core and link protein in bovine articular chondrocytes, and that this was mediated by JAK/STAT signaling. Therefore, these observations suggest a role for JAK kinase activity in cartilage homeostasis and therapeutic opportunities for JAK kinase inhibitors.

JAK family members have been implicated in additional conditions including myeloproliferative disorders (O'Sullivan et al, 2007, Mol Immunol. 44(10):2497-506), where mutations in JAK2 have been identified. This indicates that inhibitors of JAK in particular JAK2 may also be of use in the treatment of myeloproliferative disorders. Additionally, the JAK family, in particular JAK1, JAK2 and JAK3, has been linked to cancers, in particular leukaemias e.g. acute myeloid leukaemia (O'Sullivan et al, 2007, Mol Immunol. 44(10):2497-506; Xiang et al., 2008, "Identification of somatic JAK1 mutations in patients with acute myeloid leukemia" Blood First Edition Paper, prepublished online Dec. 26, 2007; DOI 10.1182/blood-2007-05-090308) and acute lymphoblastic leukaemia (Mullighan et al, 2009) or solid tumours e.g. uterine leiomyosarcoma (Constantinescu et al., 2007, Trends in Biochemical Sciences 33(3): 122-131), prostate cancer (Tam et al., 2007, British Journal of Cancer, 97, 378-383). These results indicate that inhibitors of JAK, in particular of JAK1 and/or JAK2, may also have utility in the treatment of cancers (leukaemias and solid tumours e.g. uterine leiomyosarcoma, prostate cancer).

In addition, Castleman's disease, multiple myeloma, mesangial proliferative glomerulonephritis, psoriasis, and Kaposi's sarcoma are likely due to hypersecretion of the cytokine IL-6, whose biological effects are mediated by intracellular JAK-STAT signaling (Tetsuji Naka, Norihiro Nishimoto and Tadamitsu Kishimoto, Arthritis Res 2002, 4 (suppl 3):5233-5242). This result shows that inhibitors of JAK, may also find utility in the treatment of said diseases.

The current therapies are not satisfactory and therefore there remains a need to identify further compounds that may be of use in the treatment of degenerative joint diseases, e.g. osteoarthritis, rheumatoid arthritis and osteoporosis, in particular osteoarthritis. The present invention therefore provides a compound, methods for its manufacture and pharmaceutical compositions comprising the compound of the invention together with a suitable pharmaceutical carrier. The present invention also provides for the use of the compound of the invention in the preparation of a medicament for the treatment of degenerative joint diseases. Specifically the present invention provides a novel JAK inhibitor that exhibits a dramatically improved in vivo potency.

SUMMARY OF THE INVENTION

The present invention is based on the discovery that the compound of the invention is able to act as an inhibitor of JAK and that it is useful for the treatment of inflammatory conditions, autoimmune diseases, proliferative diseases, transplantation rejection, diseases involving impairment of cartilage turnover, congenital cartilage malformations, and/or diseases associated with hypersecretion of IL6. In a specific aspect the compound is an inhibitor of JAK1 and JAK2. The present invention also provides methods for the production of this compound, a pharmaceutical composition comprising this compound and methods for treating inflammatory conditions, autoimmune diseases, proliferative diseases, transplantation rejection, diseases involving impairment of cartilage turnover, congenital cartilage malformations, and/or diseases associated with hypersecretion of IL6 by administering the compound of the invention.

Accordingly, in a first aspect of the invention, a compound of the invention is provided having a formula (I):

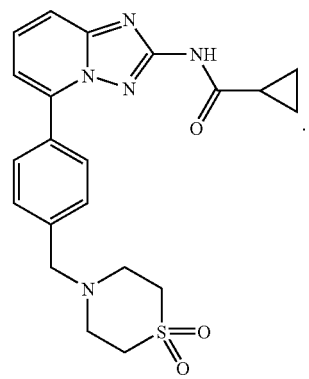

The compound of the invention is a novel inhibitor of JAK that appears to exhibit a dramatically improved in vivo potency as compared to structurally similar compounds. In a particular embodiment the compound of the invention is an inhibitor of JAK1 and JAK2. In particular it appears to exhibit this increase in potency at lower in vivo exposure levels compared to structurally similar compounds. The use of a compound with these improvements is expected to result in a lower dosage requirement (and therefore an improved dosing schedule).

In a further aspect, the present invention provides pharmaceutical compositions comprising the compound of the invention, and a pharmaceutical carrier, excipient or diluent. Moreover, the compound of the invention, useful in the pharmaceutical compositions and treatment methods disclosed herein, is pharmaceutically acceptable as prepared and used. In this aspect of the invention, the pharmaceutical composition may additionally comprise further active ingredients suitable for use in combination with the compound of the invention.

In a further aspect of the invention, this invention provides a method of treating a mammal susceptible to or afflicted with a condition from among those listed herein, and particularly, such condition as may be associated with aberrant JAK activity, e.g. inflammatory conditions, autoimmune diseases, proliferative diseases, transplantation rejection, diseases involving impairment of cartilage turnover, congenital cartilage malformations, and diseases associated with hypersecretion of IL6, which method comprises administering an effective amount of the pharmaceutical composition or compound of the invention as described herein. In a specific embodiment the condition is associated with aberrant JAK1 and JAK2 activity.

In a further aspect, the present invention provides the compound of the invention for use in the treatment or prevention of a condition selected from those listed herein, particularly such conditions as may be associated with aberrant JAK activity, e.g. inflammatory conditions, autoimmune diseases, proliferative diseases, transplantation rejection, diseases involving impairment of cartilage turnover, congenital cartilage malformations, and diseases associated with hypersecretion of IL6.

In yet another method of treatment aspect, this invention provides a method for treating a mammal susceptible to or afflicted with a condition that is causally related to abnormal JAK activity as described herein, and comprises administering an effective condition-treating or condition-preventing amount of the pharmaceutical composition or the compound of the invention described herein. In a specific aspect the condition is causally related to abnormal JAK1 and JAK2 activity.

In a further aspect, the present invention provides the compound of the invention for use in the treatment or prevention of a condition that is causally related to abnormal JAK activity.

In additional aspects, this invention provides methods for synthesizing the compound of the invention, with representative synthetic protocols and pathways disclosed later on herein.

Accordingly, it is a principal object of this invention to provide a novel compound, which can modify the activity of JAK and thus prevent or treat any maladies that may be causally related thereto. In a specific aspect the compound of the invention modulates the activity of JAK1 and JAK2.

It is further an object of this invention to provide a compound that can treat or alleviate maladies or symptoms of same, such as inflammatory conditions, autoimmune diseases, proliferative diseases, transplantation rejection, diseases involving impairment of cartilage turnover, congenital cartilage malformations, and diseases associated with hypersecretion of IL6, that may be causally related to the activity of JAK, in particular JAK1 and JAK2.

A still further object of this invention is to provide a pharmaceutical composition that may be used in the treatment or prevention of a variety of disease states, including the diseases associated with JAK activity such as inflammatory conditions, autoimmune diseases, proliferative diseases, transplantation rejection, diseases involving impairment of cartilage turnover, congenital cartilage malformations, and diseases associated with hypersecretion of IL6. In a specific embodiment the disease is associated with JAK1 and JAK2 activity.

Other objects and advantages will become apparent to those skilled in the art from a consideration of the ensuing detailed description.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term 'substituted' is to be defined as set out below. It should be further understood that the terms 'groups' and 'radicals' can be considered interchangeable when used herein.

The articles 'a' and 'an' may be used herein to refer to one or to more than one (i.e. at least one) of the grammatical objects of the article. By way of example "an analogue" means one analogue or more than one analogue.

As used herein the term 'JAK' relates to the family of Janus kinases (JAKs) which are cytoplasmic tyrosine kinases that transduce cytokine signaling from membrane receptors to STAT transcription factors. Four JAK family members are described, JAK1, JAK2, JAK3 and TYK2 and the term JAK may refer to all the JAK family members collectively or one or more of the JAK family members as the context indicates.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of the compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which the compound of the invention is administered.

'Solvate' refers to forms of the compound that are associated with a solvent, usually by a solvolysis reaction. This physical association includes hydrogen bonding. Conventional solvents include water, ethanol, acetic acid and the like. The compound of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The 'therapeutically effective amount' can vary depending on the compound, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset).

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, 'treating' or 'treatment' relates to slowing the progression of the disease.

As used herein the term 'inflammatory condition(s)' refers to the group of conditions including, rheumatoid arthritis, osteoarthritis, juvenile idiopathic arthritis, psoriasis, allergic airway disease (e.g. asthma, rhinitis), inflammatory bowel diseases (e.g. Crohn's disease, colitis), endotoxin-driven disease states (e.g. complications after bypass surgery or chronic endotoxin states contributing to e.g. chronic cardiac failure), and related diseases involving cartilage, such as that of the joints. Partcicularly the term refers to rheumatoid arthritis, osteoarthritis, allergic airway disease (e.g. asthma) and inflammatory bowel diseases.

As used herein the term 'autoimmune disease(s)' refers to the group of diseases including obstructive airways disease, including conditions such as COPD, asthma (e.g intrinsic asthma, extrinsic asthma, dust asthma, infantily asthma) particularly chronic or inveterate asthma (for example late asthma and airway hyperreponsiveness), bronchitis, including bronchial asthma, systemic lupus erythematosus (SLE), multiple sclerosis, type I diabetes mellitus and complications associated therewith, atopic eczema (atopic dermatitis), contact dermatitis and further eczematous dermatitis, inflammatory bowel disease (e.g. Crohn's disease and ulcerative colitis), atherosclerosis and amyotrophic lateral sclerosis. Particularly the term refers to COPD, asthma, systemic lupus erythematosis, type I diabetes mellitus and inflammatory bowel disease.

As used herein the term 'proliferative disease(s)' refers to conditions such as cancer (e.g. uterine leiomyosarcoma or prostate cancer), myeloproliferative disorders (e.g. polycythemia vera, essential thrombocytosis and myelofibrosis), leukemia (e.g. acute myeloid leukaemia and acute lymphoblastic leukemia), multiple myeloma, psoriasis, restenosis, sclerodermitis or fibrosis. In particular the term refers to cancer, leukemia, multiple myeloma and psoriasis.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types, such as but not limited to, melanoma, lymphoma, leukaemia, fibrosarcoma, rhabdomyosarcoma, and mastocytoma and types of tissue carcinoma, such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma.

As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML) and acute lymphoblastic leukemia (ALL).

As used herein the term 'transplantation rejection' refers to the acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases.

As used herein the term 'diseases involving impairment of cartilage turnover' includes conditions such as osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis.

As used herein the term 'congenital cartilage malformation(s)' includes conditions such as hereditary chondrolysis, chondrodysplasias and pseudochondrodysplasias, in particular, but without limitation, microtia, anotia, metaphyseal chondrodysplasia, and related disorders.

As used herein the term 'disease(s) associated with hypersecretion of IL6' includes conditions such as Castleman's disease, multiple myeloma, psoriasis, Kaposi's sarcoma and/or mesangial proliferative glomerulonephritis.

'Compound of the present invention', and equivalent expressions, are meant to embrace the compound of the Formula as hereinbefore described, which expression includes the pharmaceutically acceptable salts, and the solvates, e.g., hydrates, and the solvates of the pharmaceutically acceptable salts where the context so permits. Similarly, reference to intermediates, whether or not they themselves are claimed, is meant to embrace their salts, and solvates, where the context so permits.

Other derivatives of the compound of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985).

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compound provided herein, radioactive or not, are intended to be encompassed within the scope of the invention.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The Compound

The present invention is based on the discovery that the compound of the invention is an inhibitor of JAK and that it is useful for the treatment of inflammatory conditions, autoimmune diseases, proliferative diseases, transplantation rejection, diseases involving impairment of cartilage turnover, congenital cartilage malformations, and diseases associated with hypersecretion of IL6. The present invention also provides methods for the production of the compound of the invention, pharmaceutical compositions comprising the compound of the invention and methods for treating inflammatory conditions, autoimmune diseases, proliferative diseases, transplantation rejection, diseases involving impairment of cartilage turnover, congenital cartilage malformations, and diseases associated with hypersecretion of IL6 by administering the compound of the invention. In a specific embodiment the compound of the invention is an inhibitor of JAK1 and JAK2.

Accordingly, in a first aspect of the invention, compound of the invention is disclosed having a formula (I):

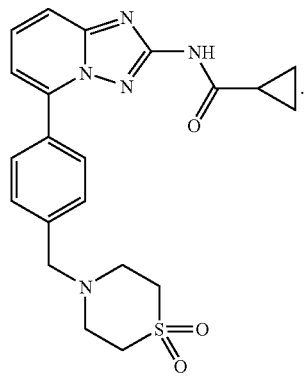

In one embodiment the compound of the invention is not an isotopic variant.

The compound of the invention is a novel inhibitor of JAK. In particular the compound is a potent inhibitor of JAK1 and JAK2, however it does inhibit TYK2 and JAK3 with a lower potency.

The compound of the invention exhibits a dramatically improved in vivo potency. This improvements are specifically and surprisingly seen even over structurally similar compounds. The use of a compound with these improvements may result in a lower dosage requirement (and therefore an improved dosing schedule).

Pharmaceutical Compositions

When employed as a pharmaceutical, the compound of this invention is typically administered in the form of a pharmaceutical composition. Such compositions can be prepared in a manner well known in the pharmaceutical art and comprise at least one active compound. Generally, the compound of this invention is administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, the compound of this invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1

Tablets

The compound of the invention may be admixed as a dry powder with a dry gelatin binder in an approximate 1:2 weight ratio. A minor amount of magnesium stearate may be added as a lubricant. The mixture may be formed into 240-270 mg tablets (80-90 mg of active amide compound per tablet) in a tablet press.

Formulation 2

Capsules

The compound of the invention may be admixed as a dry powder with a starch diluent in an approximate 1:1 weight ratio. The mixture may be filled into 250 mg capsules (125 mg of active amide compound per capsule).

Formulation 3

Liquid

The compound of the invention (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl:cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4

Tablets

The compound of the invention may be admixed as a dry powder with a dry gelatin binder in an approximate 1:2 weight ratio. A minor amount of magnesium stearate may be added as a lubricant. The mixture may be formed into 450-900 mg tablets (150-300 mg of active amide compound) in a tablet press.

Formulation 5

Injection

The compound of the invention may be dissolved or suspended in a buffered sterile saline injectable aqueous medium to a concentration of approximately 5 mg/mL.

Formulation 6

Topical

Stearyl alcohol (250 g) and a white petrolatum (250 g) may be melted at about 75° C. and then a mixture of the compound of the invention (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

The compound of the invention may be used as a therapeutic agent for the treatment of conditions in mammals that are causally related or attributable to aberrant activity of JAK. In particular, conditions related to aberrant activity of JAK1 and/or JAK2. Accordingly, the compound and pharmaceutical compositions of the invention find use as therapeutics for preventing and/or treating inflammatory conditions, autoimmune diseases, proliferative diseases, transplantation rejection, diseases involving impairment of cartilage turnover, congenital cartilage malformations, and diseases associated with hypersecretion of IL6 in mammals including humans.

In additional method of treatment aspects, this invention provides methods of treating a mammal susceptible to or afflicted with an inflammatory condition. The methods comprise administering an effective condition-treating or condition-preventing amount of one or more of the pharmaceutical compositions or compound of the invention herein described. In a specific embodiment, the inflammatory condition is selected from rheumatoid arthritis, osteoarthritis, allergic airway disease (e.g. asthma) and inflammatory bowel diseases.

In another aspect the present invention provides the compound of the invention for use in the treatment, prevention or prophylaxis of an inflammatory condition. In a specific embodiment, the inflammatory condition is selected from rheumatoid arthritis, osteoarthritis, allergic airway disease (e.g. asthma) and inflammatory bowel diseases.

In additional method of treatment aspects, this invention provides methods of treating a mammal susceptible to or afflicted with an autoimmune disease. The methods comprise administering an effective condition-treating or condition-preventing amount of one or more of the pharmaceutical compositions or compound of the invention herein described. In a specific embodiment, the autoimmune disease is selected from COPD, asthma, systemic lupus erythematosis, type I diabetes mellitus and inflammatory bowel disease.

In another aspect the present invention provides the compound of the invention for use in the treatment, prevention or prophylaxis of an autoimmune disease. In a specific embodiment, the autoimmune disease is selected from COPD, asthma, systemic lupus erythematosis, type I diabetes mellitus and inflammatory bowel disease.

In further method of treatment aspects, this invention provides methods of treating a mammal susceptible to or afflicted with a proliferative disease, in particular cancer (e.g. solid tumors such as uterine leiomyosarcoma or prostate cancer), leukemia (e.g. AML or ALL), multiple myeloma and/or psoriasis.

In another aspect the present invention provides the compound of the invention for use in the treatment, prevention or prophylaxis of a proliferative disease, in particular cancer (e.g. solid tumors such as uterine leiomyosarcoma or prostate cancer), leukemia (e.g. AML or ALL), multiple myeloma and/or psoriasis.

In further method of treatment aspects, this invention provides methods of treating a mammal susceptible to or afflicted with transplantation rejection. In a specific embodiment, the invention provides methods of treating organ transplant rejection.

In another aspect the present invention provides the compound of the invention for use in the treatment, prevention or prophylaxis of transplantation rejection In a specific embodiment, the invention provides methods of treating organ transplant rejection.

In a method of treatment aspect, this invention provides a method of treatment, prevention or prophylaxis in a mammal susceptible to or afflicted with diseases involving impairment of cartilage turnover, which method comprises administering a therapeutically effective amount of the compound of the invention, or one or more of the pharmaceutical compositions herein described.

In another aspect the present invention provides the compound of the invention for use in the treatment, prevention or prophylaxis of diseases involving impairment of cartilage turnover.

The present invention also provides a method of treatment of congenital cartilage malformations, which method comprises administering an effective amount of one or more of the pharmaceutical compositions or the compound of the invention herein described.

In another aspect the present invention provides the compound of the invention for use in the treatment, prevention or prophylaxis of congenital cartilage malformations.

In further method of treatment aspects, this invention provides methods of treating a mammal susceptible to or afflicted with diseases associated with hypersecretion of IL6, in particular Castleman's disease or mesangial proliferative glomerulonephritis.

In another aspect the present invention provides the compound of the invention for use in the treatment, prevention or prophylaxis of diseases associated with hypersecretion of IL6, in particular Castleman's disease or mesangial proliferative glomerulonephritis.

As a further aspect of the invention there is provided the compound of the invention for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

A particular regimen of the present method comprises the administration to a subject suffering from a disease involving inflammation, of an effective amount of a compound of the invention for a period of time sufficient to reduce the level of inflammation in the subject, and preferably terminate the processes responsible for said inflammation. A special embodiment of the method comprises administering of an effective amount of the compound of the invention to a subject patient suffering from or susceptible to the development of rheumatoid arthritis, for a period of time sufficient to reduce or prevent, respectively, inflammation in the joints of said patient, and preferably terminate, the processes responsible for said inflammation.

A further particular regimen of the present method comprises the administration to a subject suffering from a disease condition characterized by cartilage or joint degradation (e.g. rheumatoid arthritis and/or osteoarthritis) of an effective amount of the compound of the invention for a period of time sufficient to reduce and preferably terminate the self-perpetuating processes responsible for said degradation. A particular embodiment of the method comprises administering of an effective amount of the compound of the invention to a subject patient suffering from or susceptible to the development of osteoarthritis, for a period of time sufficient to reduce or prevent, respectively, cartilage degradation in the joints of said patient, and preferably terminate, the self-perpetuating processes responsible for said degradation. In a particular embodiment said compound may exhibit cartilage anabolic and/or anti-catabolic properties.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as degenerative conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with particular doses each providing from about 0.1 to about 10 mg/kg and especially about 1 to about 5 mg/kg.

Transdermal doses are generally selected to provide similar or lower blood levels than are achieved using injection doses.

When used to prevent the onset of an inflammatory condition, the compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compound of the invention can be administered as the sole active agent or it can be administered in combination with other therapeutic agents, including other compounds that demonstrate the same or a similar therapeutic activity, and that are determined to safe and efficacious for such combined administration. In a specific embodiment, co-administration of two (or more) agents allows for significantly lower doses of each to be used, thereby reducing the side effects seen.

In one embodiment, the compound of the invention is co-administered with another therapeutic agent for the treatment and/or prevention of a disease involving inflammation; particular agents include, but are not limited to, immunoregulatory agents e.g. azathioprine, corticosteroids (e.g. prednisolone or dexamethasone), cyclophosphamide, cyclosporin A, tacrolimus, Mycophenolate Mofetil, muromonab-CD3 (OKT3, e.g. Orthocolone®), ATG, aspirin, acetaminophen, ibuprofen, naproxen, and piroxicam.

In one embodiment, the compound of the invention is co-administered with another therapeutic agent for the treatment and/or prevention of arthritis (e.g. rheumatoid arthritis); particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, and ciclosporin), and biological DMARDS (for example but without limitation Infliximab, Etanercept, Adalimumab, Rituximab, and Abatacept).

In one embodiment, the compound of the invention is co-administered with another therapeutic agent for the treatment and/or prevention of proliferative disorders; particular agents include but are not limited to: methotrexate, leukovorin, adriamycin, prenisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin™), capecitabine, raloxifene hydrochloride, EGFR inhibitors (e.g. Iressa®, Tarceva™, Erbitux™), VEGF inhibitors (e.g. Avastin™), proteasome inhibitors (e.g. Velcade™), Glivec® and hsp90 inhibitors (e.g. 17-AAG). Additionally, a compound of the invention may be administered in combination with other therapies including, but not limited to, radiotherapy or surgery. In a specific embodiment the proliferative disorder is selected from cancer, myeloproliferative disease or leukaemia.

In one embodiment, the compound of the invention is co-administered with another therapeutic agent for the treatment and/or prevention of autoimmune diseases, particular agents include but are not limited to: glucocorticoids, cytostatic agents (e.g. purine analogs), alkylating agents, (e.g nitrogen mustards (cyclophosphamide), nitrosoureas, platinum compounds, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g., anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-β), TNF binding proteins (e.g. infliximab (Remicade™), etanercept (Enbrel™), or adalimumab (Humira™)), mycophenolate, Fingolimod and Myriocin.

In one embodiment, the compound of the invention is co-administered with another therapeutic agent for the treatment and/or prevention of transplantation rejection, particular agents include but are not limited to: calcineurin inhibitors (e.g. cyclosporin or tacrolimus (FK506)), mTOR inhibitors (e.g. sirolimus, everolimus), anti-proliferatives (e.g. azathioprine, mycophenolic acid), corticosteroids (e.g. prednisolone, hydrocortisone), Antibodies (e.g. monoclonal anti-IL-2Rα receptor antibodies, basiliximab, daclizumab), polyclonal anti-T-cell antibodies (e.g. anti-thymocyte globulin (ATG), anti-lymphocyte globulin (ALG)).

In one embodiment, the compound of the invention is co-administered with another therapeutic agent for the treatment and/or prevention of Asthma and/or Rhinitis and/or COPD, particular agents include but are not limited to: beta$_2$-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled) Long-acting β$_2$-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. ceterizine, cinnarizine, fexofenadine) and vasoconstrictors (e.g. oxymethazoline, xylomethazoline, nafazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine and intravenous magnesium sulfate.

In one embodiment, the compound of the invention is co-administered with another therapeutic agent for the treatment and/or prevention of IBD, particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and ciclosporin) and biological disease modifying, immunomodulatory agents (infliximab, adalimumab, rituximab, and abatacept).

In one embodiment, the compound of the invention is co-administered with another therapeutic agent for the treatment and/or prevention of SLE, particular agents include but are not limited to: Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid; immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, the compound of the invention is co-administered with another therapeutic agent for the treatment and/or prevention of psoriasis, particular agents include but are not limited to: topical treatments such as bath solutions, moisturizers, medicated creams and ointments containing coal tar, dithranol (anthralin), corticosteroids like desoximetasone (Topicort™), fluocinonide, vitamin D$_3$ analogues (for example, calcipotriol), Argan oiland retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive™ Enbrel™, Humira™, Remicade™, Raptiva™ and ustekinumab (a IL-12 and IL-23 blocker). Additionally, a compound of the invention may be administered in combination with other therapies including, but not limited to phototherapy, or photochemotherapy (e.g. psoralen and ultraviolet A phototherapy (PUVA)).

By co-administration is included any means of delivering two or more therapeutic agents to the patient as part of the same treatment regime, as will be apparent to the skilled person. Whilst the two or more agents may be administered simultaneously in a single formulation this is not essential. The agents may be administered in different formulations and at different times.

General Synthetic Procedures

General

The compound of the invention and the comparative examples disclosed in WO2010010190 can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of the compound of the invention as defined hereinabove and the comparative examples. The compound of the invention and the comparative examples may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 μm). Thin layer chromatography was carried out using pre-coated silica gel F-254 plates (thickness 0.25 mm) $^1$H NMR spectra were recorded on a Bruker DPX 400 NMR spectrometer (400 MHz). Chemical shifts (δ) for $^1$H NMR spectra are reported in parts per million (ppm) relative to tetramethylsilane (δ 0.00) or the appropriate residual solvent peak, i.e. $CHCl_3$ (δ 7.27), as internal reference. Multiplicities are given as singlet (s), doublet (d), triplet (t), quartet (q), multiplet (m) and broad (br). Coupling constants (J) are given in Hz. Electrospray MS spectra were obtained on a Micromass platform LC/MS spectrometer. Column Used for all LCMS analysis: Waters Acquity HPLC BEH C18 1.7 μm, 2.1 mm ID×50 mm L (Part No. 186002350)). Preparative HPLC: Waters XBridge Prep C18 5 μm ODB 19 mm ID×100 mm L (Part No. 186002978). All the methods are using $MeCN/H_2O$ gradients. $H_2O$ contains either 0.1% TFA or 0.1% $NH_3$.

List of abbreviations used in the experimental section:
DCM: Dichloromethane
DiPEA: N,N-diisopropylethylamine
MeCN Acetonitrile
BOC tert-Butyloxy-carbonyl
DMF N,N-dimethylformamide
TFA Trifluoroacetic acid
THF Tetrahydrofuran
NMR Nuclear Magnetic Resonance
DMSO Dimethylsulfoxide
DPPA Diphenylphosphorylazide
LC-MS Liquid Chromatography-Mass Spectrometry
Ppm parts-per-million
EtOAc ethyl acetate
APCI atmospheric pressure chemical ionization
Rt retention time
s singlet
br s broad singlet
m multiplet
d doublet
PdCl$_2$dppf [1,1'-Bis(diphenylphosphino)ferrocene]dichloropalladium(II)
TEA Triethylamine Synthetic Preparation of the Compound of the Invention and Comparative Examples The compound of the invention and the comparative examples can be produced according to the following scheme.

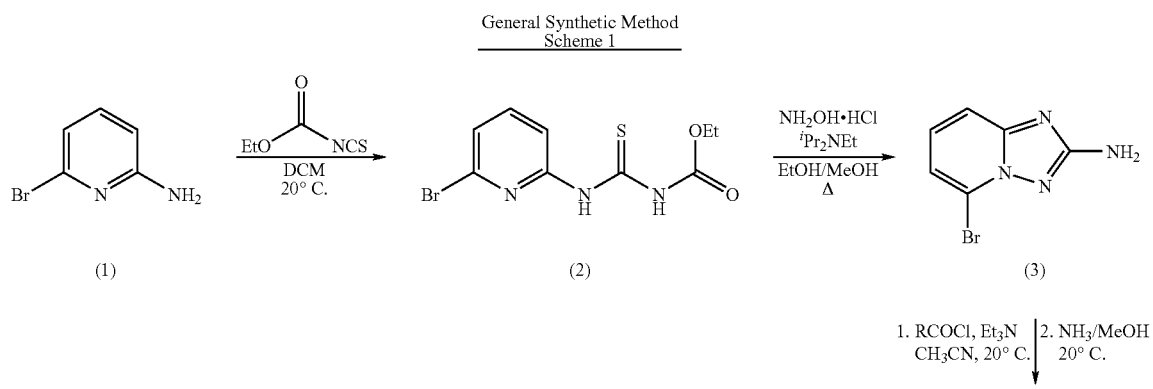

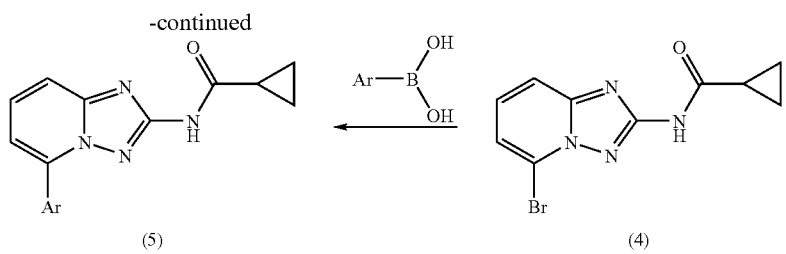

wherein Ar represents phenyl-L1-heterocycloalkyl, where L1 is a bond, —CH₂— or —CO— and the heterocycloalkyl group is optionally substituted.

General

1.1.1 1-(6-Bromo-pyridin-2-yl)-3-carboethoxy-thiourea (2)

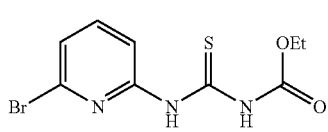

To a solution of 2-amino-6-bromopyridine (1) (253.8 g, 1.467 mol) in DCM (2.5 L) cooled to 5° C. is added ethoxycarbonyl isothiocyanate (173.0 mL, 1.467 mol) dropwise over 15 min. The reaction mixture is then allowed to warm to room temp. (20° C.) and stirred for 16 h. Evaporation in vacuo gives a solid which may be collected by filtration, thoroughly washed with petrol (3×600 mL) and air-dried to afford (2). The thiourea may be used as such for the next step without any purification. $^1$H (400 MHz, CDCl₃) δ 12.03 (1H, br s, NH), 8.81 (1H, d, J=7.8 Hz, H-3), 8.15 (1H, br s, NH), 7.60 (1H, t, J=8.0 Hz, H-4), 7.32 (1H, dd, J 7.7 and 0.6 Hz, H-5), 4.31 (2H, q, J 7.1 Hz, CH₂), 1.35 (3H, t, J 7.1 Hz, CH₃).

1.1.2 5-Bromo-[1,2,4]triazolo[1,5-a]pyridin-2-ylamine (3)

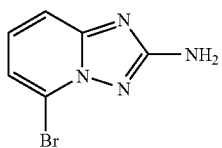

To a suspension of hydroxylamine hydrochloride (101.8 g, 1.465 mol) in EtOH/MeOH (1:1, 900 mL) is added N,N-diisopropylethylamine (145.3 mL, 0.879 mol) and the mixture is stirred at room temp. (20° C.) for 1 h. 1-(6-Bromo-pyridin-2-yl)-3-carboethoxy-thiourea (2) (89.0 g, 0.293 mol) is then added and the mixture slowly heated to reflux (Note: bleach scrubber is required to quench H₂S evolved). After 3 h at reflux, the mixture is allowed to cool and filtered to collect the precipitated solid. Further product is collected by evaporation in vacuo of the filtrate, addition of H₂O (250 mL) and filtration. The combined solids are washed successively with H₂O (250 mL), EtOH/MeOH (1:1, 250 mL) and Et₂O (250 mL) then dried in vacuo to afford the triazolopyridine derivative (3) as a solid. The compound may be used as such for the next step without any purification. $^1$H (400 MHz, DMSO-d₆) δ 7.43-7.34 (2H, m, 2×aromatic-H), 7.24 (1H, dd, J 6.8 and 1.8 Hz, aromatic-H), 6.30 (2H, br, NH₂); m/z 213/215 (1:1, M+H⁺, 100%).

1.1.3 General Procedure for Mono-Acylation to Afford Intermediate (4)

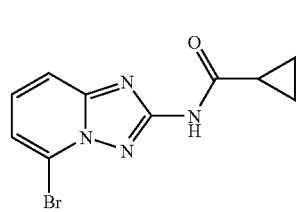

To a solution of the 2-amino-triazolopyridine (3) (7.10 g, 33.3 mmol) in dry CH₃CN (150 mL) at 5° C. is added Et₃N (11.6 mL, 83.3 mmol) followed by cyclopropanecarbonyl chloride (83.3 mmol). The reaction mixture is then allowed to warm to ambient temperature and stirred until all starting material (3) is consumed. If required, further Et₃N (4.64 mL, 33.3 mmol) and cyclopropanecarbonyl chloride (33.3 mmol) is added to ensure complete reaction. Following solvent evaporation in vacuo the resultant residue is treated with 7 N methanolic ammonia solution (50 mL) and stirred at ambient temp. (for 1-16 h) to hydrolyse any bis-acylated product. Product isolation is made by removal of volatiles in vacuo followed by trituration with Et₂O (50 mL). The solids are collected by filtration, washed with H₂O (2×50 mL), acetone (50 mL) and Et₂O (50 mL), then dried in vacuo to give the required bromo intermediate (4).

Method A

Preparation of Compounds of the Invention Via Suzuki Coupling (5):

An appropriate boronic acid (2 eq.) is added to a solution of bromo intermediate (4) in 1,4-dioxane/water (5:1). K₂CO₃ (2 eq.) and PdCl₂dppf (5%) are added to the solution. The resulting mixture is then heated in a microwave at 140° C. for 30 min (this reaction can also be carried out by traditional heating in an oil bath at 90° C. for 16 h under N₂). Water is added and the solution is extracted with ethyl acetate. The organic layers are dried over anhyd. MgSO₄ and evaporated in vacuo. The final compound is obtained after purification by flash chromatography or preparative HPLC. HPLC: Waters XBridge Prep C18 5 µm ODB 19 mm ID×100 mm L (Part No. 186002978). All the methods are using MeCN/H₂O gradients. H₂O contains either 0.1% TFA or 0.1% NH₃.

Method B

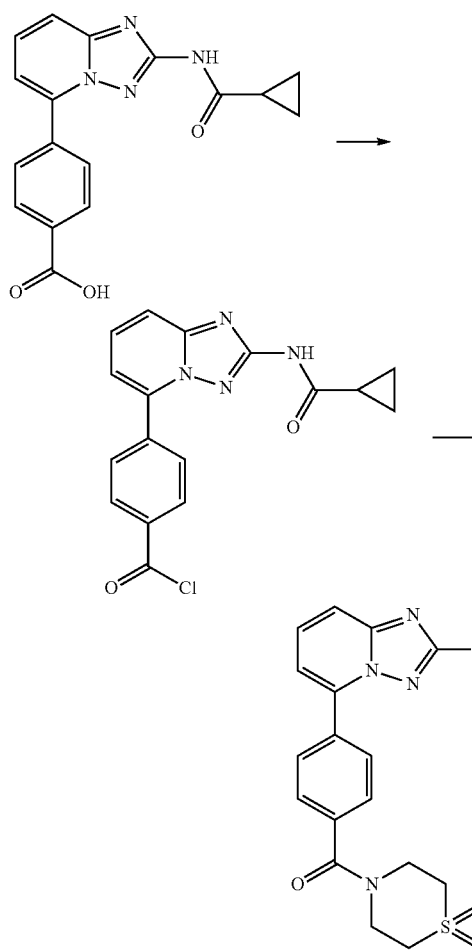

B1. 4 4-[2-(Cyclopropanecarbonyl-amino)-[1,2,4]triazolo[1,5-a]pyridin-5-yl]-benzoyl chloride

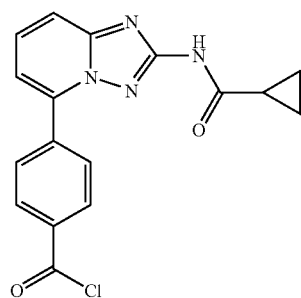

2 Drops of DMF are added to a solution of 4-[2-(cyclopropanecarbonyl-amino)-[1,2,4]triazolo[1,5-a]pyridin-5-yl]-benzoic acid (1 eq) obtained by Method A using 4-carboxyphenylboronic acid in DCM under $N_2$ atmosphere. Then oxalyl chloride (2 eq) is added dropwise to this resulting solution (gas release). The mixture is stirred at room temperature for 2 hours. After completion of the reaction by LCMS, the solvent is removed. The crude acid chloride is used without further purification in next step.

B2. Amide Formation

General Method

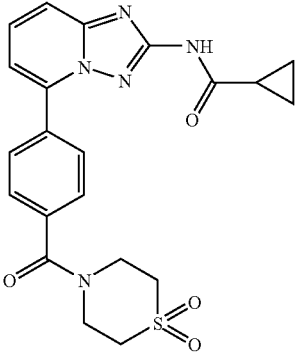

An appropriate amine (1.1 eq) and $Et_3N$ (5 eq) are dissolved in DCM under $N_2$ atmosphere and cooled at 0° C. The acid chloride (B1, 1 eq) dissolved in DCM is added dropwise to this solution. The reaction is stirred at room temperature for 16 h. After this time, reaction is complete. The compound is extracted with EtOAc and water, washed with brine and dried over anhyd. $MgSO_4$. Organic layers are filtered and evaporated. The final compound is isolated by preparative HPLC. Preparative HPLC: Waters XBridge Prep C18 5 μm ODB 19 mm ID×100 mm L (Part No. 186002978). All the methods are using $MeCN/H_2O$ gradients. $H_2O$ contains either 0.1% TFA or 0.1% $NH_3$.

Method C

Wherein $R^{3a}$ or $R^{3b}$ together with the nitrogen atom to which they are attached, may form a heterocycloalkyl.

Reductive Alkylation (General Method)

An appropriate amine (2 eq.), cyclopropanecarboxylic acid (for example cyclopropanecarboxylic acid [5-(4-formyl-phenyl)-[1,2,4]triazolo[1,5-a]pyridine-2-yl]-amide) prepared by method A (1 eq.) and Ti(OPr)$_4$ are mixed and stirred at room temperature for 3 hrs. The mixture is diluted in ethanol and Na(CN)BH$_3$ (1 eq.) is added. The resulting solution is stirred at room temperature for 16 hrs. The mixture is diluted in water and filtered. The filtrate is washed with ethanol. The combined solvent phases are evaporated under vacuum. The final compound is isolated by preparative HPLC.

Method D

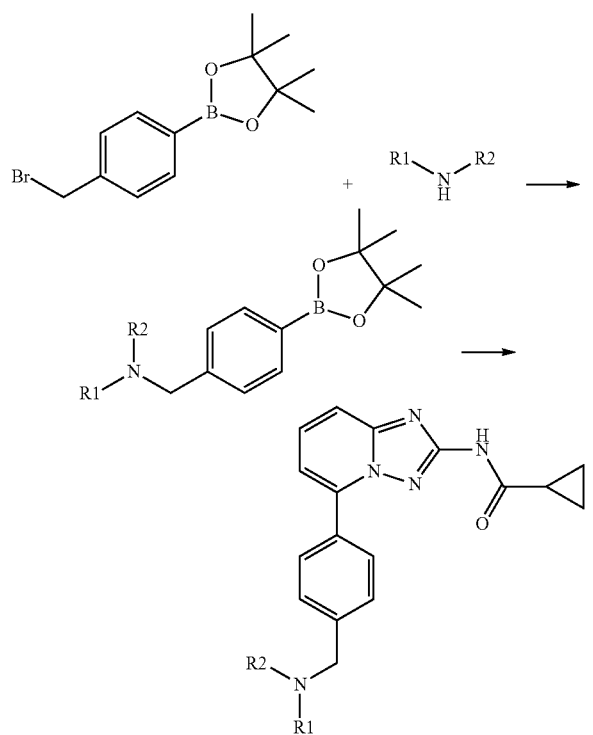

wherein R$^1$ and R$^2$ together with the Nitrogen atom to which they are attached, may form a heterocycloalkyl.

Reaction of Alkylation

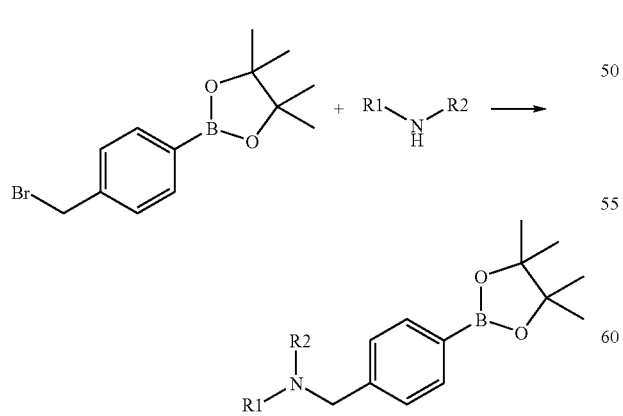

2-(4-Bromomethyl-phenyl)-4,4,5,5-tetramethyl-[1,3,2]dioxaborolane (1 eq) and Et$_3$N (2 eq) (or AgCO$_3$) are dissolved in DCM/MeOH (4:1 v:v) under N$_2$ and an amine (2 eq) is added dropwise. The resulting solution is stirred at room temperature for 16 h. After this time, the reaction is complete. The solvent is evaporated. The compound is extracted with EtOAc and water, washed with brine and dried over anhyd. MgSO$_4$. Organic layers are filtered and evaporated. The final compound is isolated by flash chromatography.

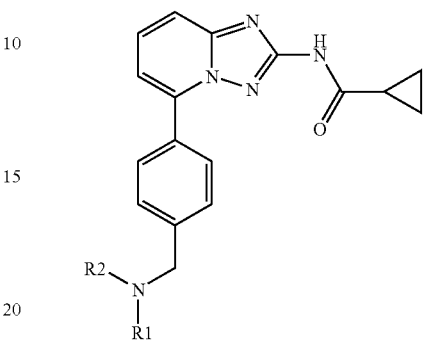

Suzuki Coupling

The obtained boronic acid (2 eq.) is added to a solution of cyclopropanecarboxylic acid (5-bromo-[1,2,4]triazolo[1,5-a]pyridin-2-yl)-amide (4) in 1,4-dioxane/water (5:1). K$_2$CO$_3$ (2 eq.) and PdCl$_2$dppf (5%) are added to the solution. The resulting mixture is then heated in a microwave at 140° C. for 30 min (This reaction can also be carried out by traditional heating in an oil bath at 90° C. for 16 h under N$_2$). Water is added and the solution is extracted with ethyl acetate. The organic layers are dried over anhyd. MgSO$_4$ and evaporated in vacuo. The final compound is obtained after purification by flash chromatography or preparative HPLC. HPLC: Waters XBridge Prep C18 5 µm ODB 19 mm ID×100 mm L (Part No. 186002978). All the methods are using MeCN/H$_2$O gradients. H$_2$O contains either 0.1% TFA or 0.1% NH$_3$.

Synthesis of the Compound of the Invention and Comparative Examples

Compound 1 (the Compound of the Invention)

Step 1:

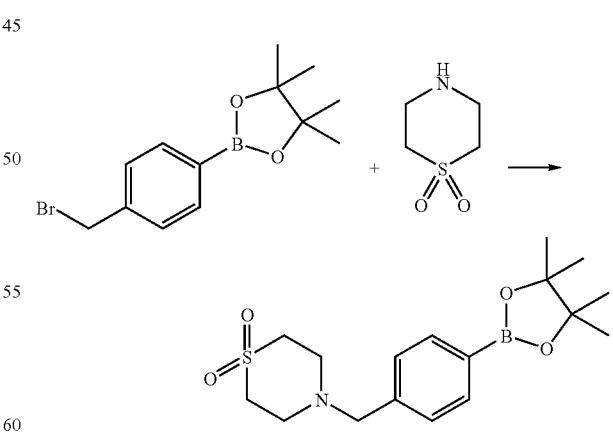

2-(4-Bromomethyl-phenyl)-4,4,5,5-tetramethyl-[1,3,2]dioxaborolane (1 eq) and DIPEA (2 eq) were dissolved in DCM/MeOH (5:1 v:v) under N$_2$ and thiomorpholine 1,1-dioxide (2 eq) was added portionwise. The resulting solution was stirred at room temperature for 16 h. After this time, the reaction was complete. The solvent was evaporated. The compound was extracted with EtOAc and water, washed with brine and dried over anhyd. MgSO₄. Organic layers were filtered and evaporated. The final compound was isolated without further purification.

Step 2: Suzuki Coupling

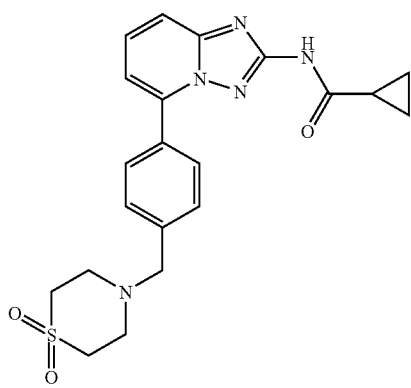

4-[4-(4,4,5,5-Tetramethyl-[1,3,2]dioxaborolan-2-yl)-benzyl]-thiomorpholine-1,1-dioxide (1.1 eq.) was added to a solution of cyclopropanecarboxylic acid (5-bromo-[1,2,4]triazolo[1,5-a]pyridin-2-yl)-amide in 1,4-dioxane/water (4:1). K₂CO₃ (2 eq.) and PdCl₂dppf (0.03 eq.) were added to the solution. The resulting mixture was then heated in an oil bath at 90° C. for 16 h under N₂. Water was added and the solution was extracted with ethyl acetate. The organic layers were dried over anhyd. MgSO₄ and evaporated in vacuo. The final compound was obtained after purification by flash chromatography.

Alternatively, after completion of the reaction, a palladium scavenger such as 1,2-bis(diphenylphosphino)ethane, is added, the reaction mixture is allowed to cooled down and a filtration is performed. The filter cake is reslurried in a suitable solvent (e.g. acetone), the solid is separated by filtration, washed with more acetone, and dried. The resulting solid is resuspended in water, aqueous HCl is added, and after stirring at RT, the resulting solution is filtered on celite (Celpure P300). Aqueous NaOH is then added to the filtrate, and the resulting suspension is stirred at RT, the solid is separated by filtration, washed with water and dried by suction. Finally the cake is re-solubilised in a mixture of THF/H₂O, treated with a palladium scavenger (e.g. SMOPEX 234) at 50° C., the suspension is filtered, the organic solvents are removed by evaporation, and the resulting slurry is washed with water and methanol, dried and sieved, to obtain the title compound as a free base.

Alternative Route to Compound 1 (the Compound of the Invention):

Step 1:

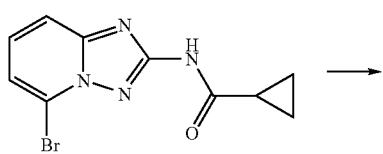

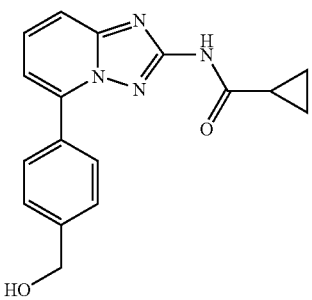

4-(Hydroxymethyl)phenylboronic acid (1.1 eq.) was added to a solution of cyclopropanecarboxylic acid (5-bromo-[1,2,4]triazolo[1,5-a]pyridin-2-yl)-amide in 1,4-dioxane/water (4:1). K₂CO₃ (2 eq.) and PdCl₂dppf (0.03 eq.) were added to the solution. The resulting mixture was then heated in an oil bath at 90° C. for 16 h under N₂. Water was added and the solution was extracted with ethyl acetate. The organic layers were dried over anhyd. MgSO₄ and evaporated in vacuo. The resulting mixture was used without further purification.

Step 2:

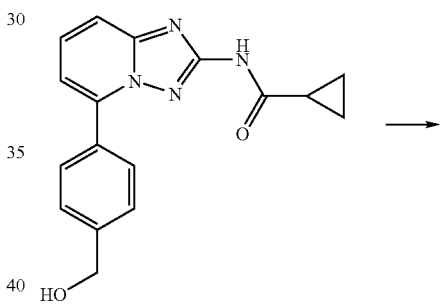

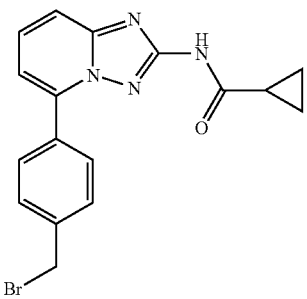

To a solution of cyclopropanecarboxylic acid [5-(4-hydroxymethyl-phenyl)-[1,2,4]triazolo[1,5-a]pyridin-2-yl]-amide (1.0 eq) in chloroform was slowly added phosphorus tribromide (1.0 equiv.). The reaction mixture was stirred at room temperature for 20 hours, quenched with ice and water (20 mL) and extracted with dichloromethane. The organic layer was dried over anhyd. MgSO₄, filtered and concentrated to dryness. The resulting white residue was triturated in dichloromethane/diethyl ether 2:1 to afford the expected product as a white solid.

Step 3:

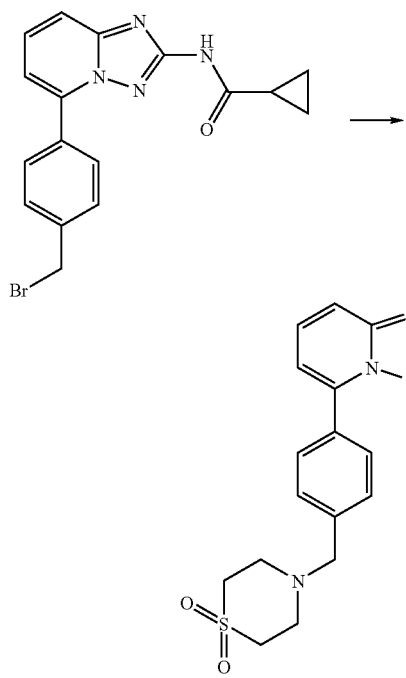

Cyclopropanecarboxylic acid [5-(4-bromomethyl-phenyl)-[1,2,4]triazolo[1,5-a]pyridin-2-yl]-amide (1 eq) and DIPEA (2 eq) were dissolved in DCM/MeOH (5:1 v:v) under $N_2$ and thiomorpholine 1,1-dioxide (1.1 eq) was added dropwise. The resulting solution was stirred at room temperature for 16 h. After this time, the reaction was complete. The solvent was evaporated. The compound was dissolved in DCM, washed with water and dried over anhyd. $MgSO_4$. Organic layers were filtered and evaporated. The final compound was isolated by column chromatography using EtOAc to afford the desired product.

COMPARATIVE EXAMPLES

Compound 2

This compound was made using General Method A and 4-[4-(4,4,5,5-tetramethyl-[1,3,2]dioxaborolan-2-yl)-benzyl]-morpholine.

Compound 3

This compound was made using General Method A and 3-(4-morpholinomethyl)-phenylboronic acid pinacol ester hydrochloride.

Compound 4

This compound was made using General Method A and 2-(4-morpholino)pyridine-5-boronic acid pinacol ester.

Compound 5

This compound was made using General Method A and 4-[4-(4,4,5,5-tetramethyl-1,3,2-dioxaborolan-2-yl)phenyl] morpholine.

Compound 6

This compound was made using General Method C and N-methyl-piperazine.

Compound 7

This compound was made using General Method C and piperidine.

Compound 8

This compound was made using General Method C and piperidine-4-carboxylic acid amide.

Compound 9

This compound was made using General Method C and 1-piperazin-1-yl-ethanone.

Compound 10

This compound was made using General Method B and thiomorpholine 1,1-dioxide.

Compound 11

This compound was made using General Method D and 4,4-difluoropiperidine.

The compound of the invention and the comparative examples that have been prepared according to the synthetic methods described herein are listed in Table I below. The NMR spectral data of the compound of the invention and some of the comparative examples is given in Table II.

TABLE I

| Cpd # | Structures | Name | MW | MS Mes'd |
|---|---|---|---|---|
| 1 | 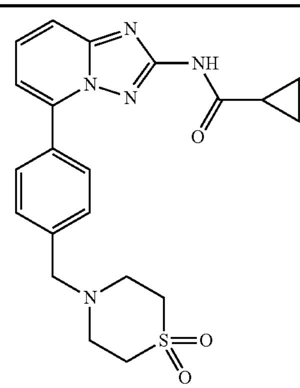 | Cyclopropanecarboxylic acid {5-[4-(1,1-dioxo-1-thiomorpholin-4-ylmethyl)-phenyl]-[1,2,4]triazolo[1,5-a]pyridin-2-yl}-amide | 425.51 | 426 |

TABLE I-continued

| Cpd # | Structures | Name | MW | MS Mes'd |
|---|---|---|---|---|
| 2 | 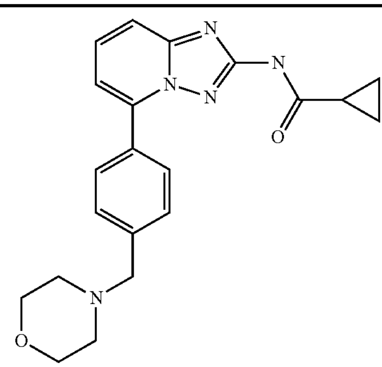 | N-(5-(4-(morpholinomethyl)phenyl)-[1,2,4]triazolo[1,5-a]pyridin-2-yl)cyclopropanecarboxamide | 377.45 | 378.20 |
| 3 | 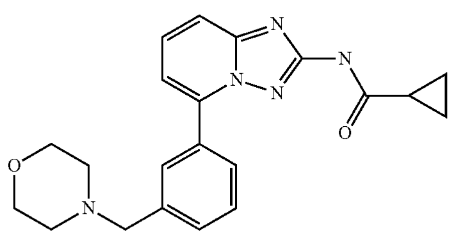 | N-(5-(3-(morpholinomethyl)phenyl)-[1,2,4]triazolo[1,5-a]pyridin-2-yl)cyclopropanecarboxamide | 377.45 | 378.20 |
| 4 | 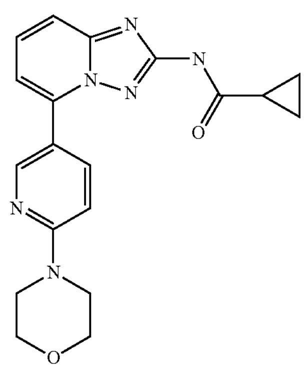 | N-(5-(6-morpholinopyridin-3-yl)-[1,2,4]triazolo[1,5-a]pyridin-2-yl)cyclopropanecarboxamide | 364.41 | 365.10 |
| 5 | 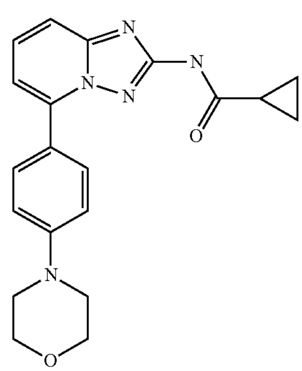 | N-(5-(4-morpholinophenyl)-[1,2,4]triazolo[1,5-a]pyridin-2-yl)cyclopropanecarboxamide | 363.42 | 364.0 |

TABLE I-continued

| Cpd # | Structures | Name | MW | MS Mes'd |
|---|---|---|---|---|
| 6 | 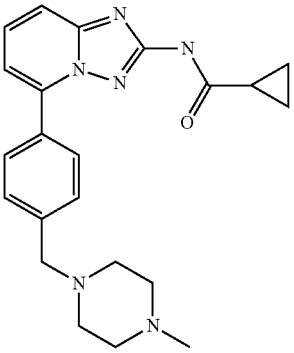 | N-(5-(4-((4-methylpiperazin-1-yl)methyl)phenyl)-[1,2,4]triazolo[1,5-a]pyridin-2-yl)cyclopropanecarboxamide | 390;49 | 391.1 |
| 7 | 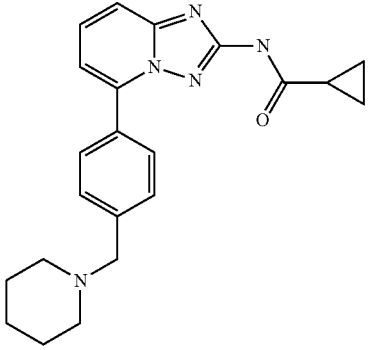 | N-(5-(4-(piperidin-1-ylmethyl)phenyl)-[1,2,4]triazolo[1,5-a]pyridin-2-yl)cyclopropanecarboxamide | 375.48 | 376.1 |
| 8 | 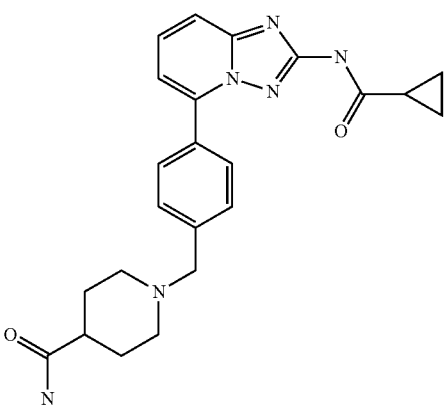 | 1-(cyclopropanecarboxamido)-[1,2,4]triazolo[1,5-a]pyridin-5-yl)benzyl)piperidine-4-carboxamide | 418.5 | 419.1 |
| 9 | 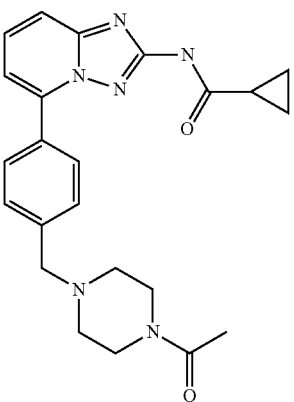 | N-(5-(4-((4-acetoylpiperazin-1-yl)methyl)phenyl)-[1,2,4]triazolo[1,5-a]pyridin-2-yl)cyclopropanecarboxamide | 418.5 | 419.1 |

TABLE I-continued

| Cpd # | Structures | Name | MW | MS Mes'd |
|---|---|---|---|---|
| 10 | 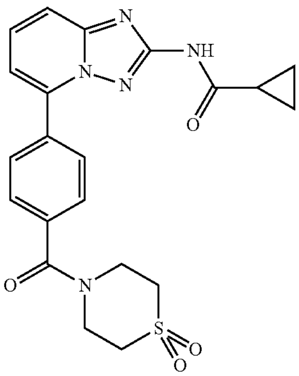 | Cyclopropanecarboxylic acid {5-[4-(1,1-dioxo-1-thiomorpholine-4-carbonyl)-phenyl]-[1,2,4]triazolo[1,5-a]pyridin-2-yl}-amide | 439.49 | 440.0 |
| 11 | 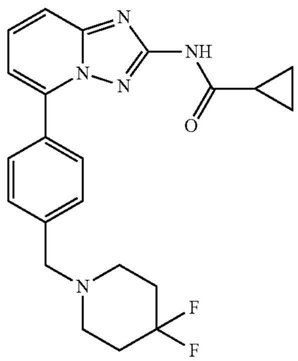 | Cyclopropanecarboxylic acid {5-[4-(4,4-difluoro-piperidin-1-ylmethyl)-phenyl]-[1,2,4]triazolo[1,5-a]pyridin-2-yl}-amide | 411.46 | 412.1 |

TABLE II

NMR Data of Representative Compounds of the Invention

| Cpd # | (δ) NMR data |
|---|---|
| 1 | ($^1$H, DMSO-d6) 11.00 (1H, b, NH) 7.99 (2H, d, 2xArH) 7.70 (2H, m, 2xArH) 7.53 (2H, d, 2xArH) 7.30 (1H, dd, ArH) 3.78 (2H, s, CH$_2$) 3.14 (4H, b, 4xCH) 2.93 (4H, b, 4xCH) 2.03 (1H, b, CH) 0.82 (4H, m, 2xCH$_2$) |
| 2 | ($^1$H, CDCl$_3$) 10.20 (1H, b, NH), 8.06 (2H, d, ArH), 7.72 (2H, m, ArH), 7.63 (2H, d, ArH), 7.23 (1H, d, ArH), 4.27 (2H, s, CH$_2$), 3.99 (4H, m, 2xCH$_2$), 3.50 (2H, br, CH$_2$), 2.95 (2H, br, CH$_2$), 1.97 (1H, br, CH), 1.17 (2H, m, CH$_2$), 0.95 (2H, m, CH$_2$) |
| 3 | ($^1$H, CDCl$_3$) 8.32 (1H, s, ArH), 7.96 (1H, m, ArH), 7.79 (1H, m, ArH), 7.66 (3H, m, ArH), 7.32 (1H, d, ArH), 4.31 (2H, s, CH$_2$), 4.05 (4H, b, 2xCH$_2$), 3.6 (2H, br, CH$_2$), 3.06 (2H, br, CH$_2$), 1.85 (1H, br, CH), 1.12 (2H, m, CH$_2$), 0.98 (2H, m, CH$_2$) |
| 4 | ($^1$H, CDCl$_3$) 8.71 (1H, s, NH), 8.35 (1H, m, ArH), 8.27 (1H, br, ArH), 7.57 (2H, d, ArH), 7.07 (1H, m, ArH), 6.78 (1H, d, ArH), 3.86 (4H, m, 2xCH$_2$), 3.66 (4H, m, 2xCH$_2$), 1.6 (1H, br, CH), 1.22 (2H, m, CH$_2$), 0.95 (2H, m, CH$_2$) |
| 5 | ($^1$H, DMSO-d6) 11.06 (1H, br, NH), 7.98 (2H, d, ArH), 7.67 (1H, m, ArH), 7.59 (1H, d, ArH), 7.25 (1H, m, ArH), 7.08 (2H, m, ArH), 3.67 (4H, m, 2xCH$_2$), 3.25 (4H, m, 2xCH$_2$), 2.02 (1H, br, CH), 0.82 (4H, m, 2xCH$_2$) |
| 10 | ($^1$H, DMSO-d6) 11.03 (1H, b, NH), 8.11 (2H, d, ArH), 7.73 (1H, d, ArH), 7.72 (1H, s, ArH), 7.68 (2H, d, ArH), 7.36 (1H, dd, ArH), 4.01 (2H, b, CH2), 3.81 (2H, b, CH$_2$), 3.31 (4H, b under water peak, 2xCH$_2$), 2.03 (1H, b, CH), 0.81 (4H, m, CH$_2$). |
| 11 | ($^1$H, DMSO-d6) 10.99 (1H, b, NH), 7.98 (2H, d, 2xArH), 7.70 (2H, m, 2xArH), 7.50 (2H, d, 2xArH), 7.29 (1H, dd, ArH), 3.65 (2H, s, CH$_2$), 2.54 (4H, b, 4xCH), 1.98 (5H, b, 5xCH), 0.81 (4H, m, 2xCH$_2$) |

BIOLOGICAL EXAMPLES

Example 1

In-Vitro Assays 1.1 JAK1 Inhibition Assay

Recombinant human JAK1 catalytic domain (amino acids 850-1154; catalog number 08-144) was purchased from Carna Biosciences. 10 ng of JAK1 was incubated with 12.5 µg polyGT substrate (Sigma catalog number P0275) in kinase reaction buffer (15 mM Tris-HCl pH 7.5, 1 mM DTT, 0.01% Tween-20, 10 mM MgCl$_2$, 2 µM non-radioactive ATP, 0.25 µCi $^{33}$P-gamma-ATP (GE Healthcare, catalog number AH9968) final concentrations) with or without 5 µL containing test compound or vehicle (DMSO, 1% final concentration), in a total volume of 25 µL, in a polypropylene 96-well plate (Greiner, V-bottom). After 45 min at 30° C., reactions were stopped by adding of 25 µL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 µL per well of a 75 mM phosphoric acid solution and the bottom of the plates was sealed. 40 µL/well of Microscint-20 was added, the top of the plates was sealed and readout was performed using the Topcount (Perkin Elmer). Kinase activity was calculated by subtracting counts per minute (cpm) obtained in the presence of a positive control inhibitor (10 µM staurosporine) from cpm obtained in the presence of vehicle. The ability of a test compound to inhibit this activity was determined as:

Percentage inhibition=((cpm determined for sample with test compound present–cpm determined for sample with positive control inhibitor) divided by (cpm determined in the presence of vehicle–cpm determined for sample with positive control inhibitor))*100.

Dose dilution series were prepared for the compounds enabling the testing of dose-response effects in the JAK1 assay and the calculation of the $IC_{50}$ for each compound. Each compound was routinely tested at concentration of 20 µM followed by a 1/3 serial dilution, 8 points (20 µM-6.67 µM-2.22 µM-740 nM-247 nM-82 nM-27 nM-9 nM) in a final concentration of 1% DMSO. When potency of compound series increased, more dilutions were prepared and/or the top concentration was lowered (e.g. 5 µM, 1 µM).

The following compounds have been tested for their activity against JAK1 and the $IC_{50}$ values, as determined using the assays described herein, are given below in Table IIIA.

TABLE IIIA

JAK1 Values of Compounds

| Cpd # | JAK1 $IC_{50}$ (nM) |
|---|---|
| 1 | 47.07, 55.66, 50.1, 48.29 |
| 2 | 50.91, 52.11 |
| 3 | 291 |
| 4 | 1032 |
| 5 | 1450 |
| 6 | 3448 |
| 7 | 504.1 |
| 8 | 435 |
| 9 | 334.3 |
| 10 | 18.16 |
| 11 | 7.69 |

1.2 JAK1 Ki Determination Assay

For the determination of Ki, different amounts of compound were mixed with the enzyme and the enzymatic reaction was followed as a function of ATP concentration. The Ki was determined by means of double reciprocal plotting of Km vs compound concentration (Lineweaver-Burk plot). 1 ng of JAK1 (Invitrogen, PV4774) was used in the assay. The substrate was 50 nM Ulight-JAK-1 (Tyr1023) Peptide (Perkin Elmer, TRF0121) The reaction was performed in 25 mM MOPS pH 6.8, 0.01%, 2 mM DTT, 5 mM $MgCl_2$ Brij-35 with varying concentrations of ATP and compound. Phosphorylated substrate was measured using an Eu-labeled anti-phosphotyrosine antibody PT66 (Perkin Elmer, AD0068). Readout was performed on the envision (Perkin Elmer) with excitation at 320 nm and emission followed at 615 nm and 665 nm.

For example, when Compound 1 was tested in this assay, a Ki value of 39 nM was measured.

1.3 JAK2 Inhibition Assay

Recombinant human JAK2 catalytic domain (amino acids 808-1132; catalog number PV4210) was purchased from Invitrogen. 0.025 mU of JAK2 was incubated with 2.5 µg polyGT substrate (Sigma catalog number P0275) in kinase reaction buffer (5 mM MOPS pH 7.5, 9 mM MgAc, 0.3 mM EDTA, 0.06% Brij and 0.6 mM DTT, 1 µM non-radioactive ATP, 0.25 µCi $^{33}$P-gamma-ATP (GE Healthcare, catalog number AH9968) final concentrations) with or without 5 µL containing test compound or vehicle (DMSO, 1% final concentration), in a total volume of 25 µL, in a polypropylene 96-well plate (Greiner, V-bottom). After 90 min at 30° C., reactions were stopped by adding of 25 µL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 µL per well of a 75 mM phosphoric acid solution and the bottom of the plates was sealed. 40 µL/well of Microscint-20 was added, the top of the plates was sealed and readout was performed using the Topcount (Perkin Elmer). Kinase activity was calculated by subtracting counts per minute (cpm) obtained in the presence of a positive control inhibitor (10 µM staurosporine) from cpm obtained in the presence of vehicle. The ability of a test compound to inhibit this activity was determined as:

Percentage inhibition=((cpm determined for sample with test compound present–cpm determined for sample with positive control inhibitor) divided by (cpm determined in the presence of vehicle–cpm determined for sample with positive control inhibitor))*100.

Dose dilution series were prepared for the compounds enabling the testing of dose-response effects in the JAK2 assay and the calculation of the $IC_{50}$ for each compound. Each compound was routinely tested at concentration of 20 µM followed by a 1/3 serial dilution, 8 points (20 µM-6.67 µM-2.22 µM-740 nM-247 nM-82 nM-27 nM-9 nM) in a final concentration of 1% DMSO. When potency of compound series increased, more dilutions were prepared and/or the top concentration was lowered (e.g. 5 µM, 1 µM).

The following compounds have been tested for their activity against JAK2 and the $IC_{50}$ values, as determined using the assays described herein, are given below in Table IIIB

TABLE IIIB

JAK2 $IC_{50}$ Values of Compounds

| Cpd # | JAK2 $IC_{50}$ (nM) |
|---|---|
| 1 | 31.37, 41.16, 55.49, 167.34 |
| 2 | 38.73, 152.3, 184.7 |
| 3 | N/A |
| 4 | N/A |
| 5 | 1760 |
| 6 | 5070 |
| 7 | 6449 |
| 8 | 7731, 1355 |
| 9 | 848.7 |
| 10 | 65.42 |
| 11 | 15.51 |

1.4 JAK2 Kd Determination Assay

JAK2 (Invitrogen, PV4210) was used at a final concentration of 5 nM. The binding experiment was performed in 50 mM Hepes pH 7.5, 0.01% Brij-35, 10 mM $MgCl_2$, 1 mM EGTA using 25 nM kinase tracer 236 (Invitrogen, PV5592) and 2 nM Eu-anti-GST (Invitrogen, PV5594) with varying compound concentrations. Detection of tracer was performed according to the manufacturers procedure.

For example, when Compound 1 was tested in this assay, a Kd value of 205 nM was measured.

1.5 JAK3 Inhibition Assay

Recombinant human JAK3 catalytic domain (amino acids 781-1124; catalog number PV3855) was purchased from Invitrogen. 0.025 mU of JAK3 was incubated with 2.5 μg polyGT substrate (Sigma catalog number P0275) in kinase reaction buffer (25 mM Tris pH 7.5, 0.5 mM EGTA, 0.5 mM $Na_3VO_4$, 5 mM b-glycerolphosphate, 0.01% Triton X-100, 1 μM non-radioactive ATP, 0.25 μCi 33P-gamma-ATP (GE Healthcare, catalog number AH9968) final concentrations) with or without 5 μL containing test compound or vehicle (DMSO, 1% final concentration), in a total volume of 25 μL, in a polypropylene 96-well plate (Greiner, V-bottom). After 105 min at 30° C., reactions were stopped by adding of 25 μL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 μL per well of a 75 mM phosphoric acid solution and the bottom of the plates was sealed. 40 μL/well of Microscint-20 was added, the top of the plates was sealed and readout was performed using the Topcount (Perkin Elmer). Kinase activity was calculated by subtracting counts per minute (cpm) obtained in the presence of a positive control inhibitor (10 μM staurosporine) from cpm obtained in the presence of vehicle. The ability of a test compound to inhibit this activity was determined as:

Percentage inhibition=((cpm determined for sample with test compound present−cpm determined for sample with positive control inhibitor) divided by (cpm determined in the presence of vehicle−cpm determined for sample with positive control inhibitor))*100.

Dose dilution series were prepared for the compounds enabling the testing of dose-response effects in the JAK3 assay and the calculation of the $IC_{50}$ for each compound. Each compound was routinely tested at concentration of 20 μM followed by a 1/3 serial dilution, 8 points (20 μM-6.67 μM-2.22 μM-740 nM-247 nM-82 nM-27 nM-9 nM) in a final concentration of 1% DMSO. When potency of compound series increased, more dilutions were prepared and/or the top concentration was lowered (e.g. 5 μM, 1 μM).

The following compounds have been tested for their activity against JAK3 and the $IC_{50}$ values, as determined using the assays described herein, are given below in Table IIIC.

TABLE IIIC

JAK3 $IC_{50}$ Values of Compounds

| Cpd # | JAK3 $IC_{50}$ (nM) |
|---|---|
| 1 | 149.35, 187.3, 189.3, 194.7 |
| 2 | 2843 |
| 11 | 194.6 |

1.6 JAK3 Ki Determination Assay

For the determination of Ki, different amounts of compound are mixed with the enzyme and the enzymatic reaction is followed as a function of ATP concentration. The Ki is determined by means of double reciprocal plotting of Km vs compound concentration (Lineweaver-Burk plot). JAK3 (Carna Biosciences, 09CBS-0625B) was used at a final concentration of 10 ng/ml. The substrate was Poly(Glu,Tyr)sodium salt (4:1), MW 20 000-50 000 (Sigma, P0275) The reaction was performed in 25 mM Tris pH 7.5, 0.01% Triton X-100, 0.5 mM EGTA, 2.5 mM DTT, 0.5 mM $Na_3VO_4$, 5 mM b-glycerolphosphate, 10 mM $MgCl_2$ with varying concentrations of ATP and compound and stopped by addition of 150 mM phosphoric acid. Measurement of incorporated phosphate into the substrate polyGT was done by loading the samples on a filter plate (using a harvester, Perkin Elmer) and subsequent washing. Incorporated $^{33}P$ in polyGT is measured in a Topcount scintillation counter after addition of scintillation liquid to the filter plates (Perkin Elmer).

For example, when Compound 1 was tested in this assay, a Ki value of 353 nM was measured.

1.7 TYK2 Inhibition Assay

Recombinant human TYK2 catalytic domain (amino acids 871-1187; catalog number 08-147) was purchased from Carna biosciences. 5 ng of TYK2 was incubated with 12.5 μg polyGT substrate (Sigma catalog number P0275) in kinase reaction buffer (25 mM Hepes pH 7.5, 100 mM NaCl, 0.2 mM $Na_3VO_4$, 0.1% NP-40, 0.1 μM non-radioactive ATP, 0.125 μCi $^{33}P$-gamma-ATP (GE Healthcare, catalog number AH9968) final concentrations) with or without 5 μL containing test compound or vehicle (DMSO, 1% final concentration), in a total volume of 25 μL, in a polypropylene 96-well plate (Greiner, V-bottom). After 90 min at 30° C., reactions were stopped by adding 25 μL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 μL per well of a 75 mM phosphoric acid solution and the bottom of the plates was sealed. 40 μL/well of Microscint-20 was added, the top of the plates was sealed and readout was performed using the Topcount (Perkin Elmer). Kinase activity was calculated by subtracting counts per minute (cpm) obtained in the presence of a positive control inhibitor (10 μM staurosporine) from cpm obtained in the presence of vehicle. The ability of a test compound to inhibit this activity was determined as:

Percentage inhibition=((cpm determined for sample with test compound present−cpm determined for sample with positive control inhibitor) divided by (cpm determined in the presence of vehicle−cpm determined for sample with positive control inhibitor))*100.

Dose dilution series were prepared for the compounds enabling the testing of dose-response effects in the TYK2 assay and the calculation of the $IC_{50}$ for each compound. Each compound was routinely tested at concentration of 20 μM followed by a 1/3 serial dilution, 8 points (20 μM-6.67 μM-2.22 μM-740 nM-247 nM-82 nM-27 nM-9 nM) in a final concentration of 1% DMSO. When potency of compound series increased, more dilutions were prepared and/or the top concentration was lowered (e.g. 5 μM, 1 μM).

The following compounds have been tested for their activity against TYK2; and the $IC_{so}$ values, as determined using the assays described herein, are given below in Table IIID.

TABLE IIID

TYK2 $IC_{50}$ Values of Compounds

| Cpd # | TYK2 $IC_{50}$ (nM) |
|---|---|
| 1 | 72.7, 73.75, 79.07, 86.77 |
| 2 | 2096 |
| 11 | 125.8 |

1.8 TYK2 Kd Determination Assay

TYK2 (Calm Biosciences, 09CBS-0983D) was used at a final concentration of 5 nM. The binding experiment was performed in 50 mM Hepes pH 7.5, 0.01% Brij-35, 10 mM $MgCl_2$, 1 mM EGTA using 50 nM kinase tracer 236 (Invitrogen, PV5592) and 2 nM Eu-anti-GST (Invitrogen, PV5594) with varying compound concentrations. Detection of tracer was performed according to the manufacturers' procedure.

For example, when Compound 1 was tested in this assay, a Kd value of 376 nM was measured.

Example 2

Cellular Assays 2.1 JAK-STAT Signalling Assay:

HeLa cells were maintained in Dulbecco's Modified Eagle's Medium (DMEM) containing 10% heat inactivated fetal calf serum, 100 U/mL penicillin and 100 µg/mL streptomycin. HeLa cells were used at 70% confluence for transfection. 20,000 cells in 87 µL cell culture medium were transiently transfected with 40 ng pSTAT1(2)-luciferase reporter (Panomics), 8 ng of LacZ reporter as internal control reporter and 52 ng of pBSK using 0.32 µL Jet-PEI (Polyplus) as transfection reagent per well in 96-well plate format. After overnight incubation at 37° C., 10% $CO_2$, transfection medium was removed. 75 µL of DMEM+1.5% heat inactivated fetal calf serum was added. 15 µL compound at 6.7× concentration was added for 60 min and then 10 µL of human OSM (Peprotech) at 33 ng/mL final concentration.

All compounds were tested in duplicate starting from 20 µM followed by a 1/3 serial dilution, 8 doses in total (20 µM-6.6 µM-2.2 µM-740 nM-250 nM-82 nM-27 nM-9 nM) in a final concentration of 0.2% DMSO.

After overnight incubation at 37° C., 10% $CO_2$ cells were lysed in 100 µL lysis buffer/well (PBS, 0.9 mM $CaCl_2$, 0.5 mM $MgCl_2$, 5% Trehalose, 0.025% Tergitol NP9, 0.15% BSA).

40 µL of cell lysate was used to read β-galactosidase activity by adding 180 µL β-Gal solution (30 µl ONPG 4 mg/mL+ 150 µL β-Galactosidase buffer (0.06 M $Na_2HPO_4$, 0.04 M $NaH_2PO_4$, 1 mM $MgCl_2$)) for 20 min. The reaction was stopped by addition of 50 µL $Na_2CO_3$ 1 M. Absorbance was read at 405 nm.

Luciferase activity was measured using 40 µL cell lysate plus 40 µL of Steadylite® as described by the manufacturer (Perkin Elmer), on the Envision (Perkin Elmer).

10 µM of a pan-JAK inhibitor was used as a positive control (100% inhibition). As negative control 0.5% DMSO (0% inhibition) was used. The positive and negative controls were used to calculate z' and 'percent inhibition' (PIN) values.

> Percentage inhibition=((fluorescence determined in the presence of vehicle–fluorescence determined for sample with test compound present) divided by (fluorescence determined in the presence of vehicle–fluorescence determined for sample without trigger))*100.

PIN values were plotted for compounds tested in dose-response and $EC_{50}$ values were derived.

TABLE IV

| Cpd # | $EC_{50}$ (nM) |
|---|---|
| 1 | 922.5, 625.6, 987.7, 1767 |
| 2 | >10000, 3322, 2492 |
| 11 | 740.4 |

Example 2.2

OSM/IL-1β Signaling Assay

OSM and IL-1β were shown to synergistically upregulate MMP13 levels in the human chondrosarcoma cell line SW1353. The cells were seeded in 96 well plates at 15,000 cells/well in a volume of 120 µL DMEM (Invitrogen) containing 10% (v/v) FBS and 1% penicillin/streptomycin (InVitrogen) incubated at 37° C. 5% $CO_2$. Cells were preincubated with 15 µL of compound in M199 medium with 2% DMSO 1 hr before triggering with 15 µL OSM and IL-1β to reach 25 ng/mL OSM and 1 ng/mL IL-1β, and MMP13 levels were measured in conditioned medium 48 hours after triggering. MMP13 activity was measured using an antibody capture activity assay. For this purpose, 384 well plates (NUNC, 460518, MaxiSorb black) were coated with 35 µL of a 1.5 µg/mL anti-human MMP13 antibody (R&D Systems, MAB511) solution for 24 hrs at 4° C. After washing the wells 2 times with PBS+0.05% Tween, the remaining binding sites were blocked with 100 µL 5% non-fat dry milk (Santa Cruz, sc-2325, Blotto) in PBS for 24 hr at 4° C. Next, the wells were washed twice with PBS+0.05% Tween and 35 µL of 1/10 dilution of culture supernatant containing MMP13 in 100-fold diluted blocking buffer was added and incubated for 4 hr at room temperature. Next the wells were washed twice with PBS+0.05% Tween followed by MMP13 activation by addition of 35 µL of a 1.5 mM 4-Aminophenylmercuric acetate (APMA) (Sigma, A9563) solution and incubation at 37° C. for 1 hr. The wells were washed again with PBS+0.05% Tween and 35 µL MMP13 substrate (Biomol, P-126, OmniMMP fluorogenic substrate) was added. After incubation for 24 hrs at 37° C. fluorescence of the converted substrate was measured in a Perkin Elmer Wallac EnVision 2102 Multilabel Reader (wavelength excitation: 320 nm, wavelength emission: 405 nm).

> Percentage inhibition=((fluorescence determined in the presence of vehicle–fluorescence determined for sample with test compound present) divided by (fluorescence determined in the presence of vehicle–fluorescence determined for sample without trigger))*100.

For example, when Compound 1 was tested in this assay, an $EC_{50}$ value of 2242.5 (±1098.5) nM was measured.

Example 2.3

PBL Proliferation Assay

Human peripheral blood lymphocytes (PBL) are stimulated with IL-2 and proliferation is measured using a BrdU incorporation assay. The PBL are first stimulated for 72 hrs with PHA to induce IL-2 receptor, then they are fasted for 24 hrs to stop cell proliferation followed by IL-2 stimulation for another 72 hrs (including 24 hr BrdU labeling). Cells are preincubated with test compounds 1 hr before IL-2 addition. Cells are cultured in RPMI 1640 containing 10% (v/v) FBS.

Example 2.4

Whole Blood Assay (WBA)

2.4.1 IFNα Stimulation Protocol

To predict the potency of the test compounds to inhibit JAK1 or JAK2-dependent signaling pathways in vivo, a physiologically relevant in vitro model was developed using human whole blood. In the WBA assay, blood, drawn from human volunteers who gave informed consent, was treated ex vivo with compound (1 h) and subsequently stimulated either for 30 minutes with interferon α (IFNα, JAK1 dependent pathway) or for 2 h with granulocyte macrophage-colony stimulating factor (GM-CSF, JAK2 dependent pathway).

2.4.1.1 Phospho-STAT1 Assay

For IFNα stimulation, increase in phosphorylation of Signal Transducers and Activators of Transcription 1 (pSTAT1) by INFα in white blood cell extracts was measured using a pSTAT1 ELISA assay. Phosphorylation of Signal Transducer and Activator of Transcription 1 (STAT1) after interferon alpha (IFNα) triggering is a JAK1-mediated event. The Phospho-STAT1 Assay, which was used to measure Phospho-STAT1 levels in cellular extracts, was developed to assess the ability of a compound to inhibit JAK1-dependent signaling pathways.

Whole human blood, drawn from human volunteers who gave informed consent, was ex vivo treated with compound (1 h) and subsequently stimulated for 30 minutes with IFNα. The increase in phosphorylation of STAT1 by INFα in white blood cell extracts was measured using a phospho-STAT1 ELISA.

The ACK lysis buffer consisted of 0.15 M $NH_4Cl$, 10 mM $KHCO_3$, 0.1 mM EDTA. The pH of the buffer was 7.3.

A 10× cell lysis buffer concentrate (part of the PathScan Phospho-STAT1 (Tyr701) sandwich ELISA kit from Cell Signaling) was diluted 10-fold in $H_2O$. Proteinase inhibitors were added to the buffer before use.

20 µg IFNα is dissolved in 40 µL $H_2O$ to obtain a 500 µg/mL stock solution. The stock solution was stored at −20° C.

A 3-fold dilution series of the compound was prepared in DMSO (highest concentration: 10 mM). Subsequently, the compound was further diluted in medium (dilution factor dependent on desired final compound concentration).

2.4.1.1.1 Incubation of Blood with Compound and Stimulation with IFNα

Human blood was collected in heparinized tubes. The blood was divided in aliquots of 392 µL. Afterwards, 4 µL of compound dilution was added to each aliquot and the blood samples were incubated for 1 h at 37° C. The IFNα stock solution was diluted 1000-fold in RPMI medium to obtain a 500 ng/mL working solution. 4 µL of the 500 ng/mL work solution was added to the blood samples (final concentration IFNα: 5 ng/ml). The samples were incubated at 37° C. for 30 min.

2.4.1.1.2 Preparation of Cell Extracts

At the end of the stimulation period, 7.6 mL ACK buffer was added to the blood samples to lyse the red blood cells. The samples were mixed by inverting the tubes five times and the reaction was incubated on ice for 5 min. The lysis of the RBC should be evident during this incubation. The cells were pelleted by centrifugation at 300 g, 4° C. for 7 min and the supernatant was removed. 10 mL 1×PBS was added to each tube and the cell pellet was resuspended. The samples were centrifuged again for 7 min at 300 g, 4° C. The supernatant was removed and the pellet resuspended in 500 µL of 1×PBS. Then, the cell suspension was transferred to a clean 1.5 mL microcentrifuge tube. The cells were pelleted by centrifugation at 700 g for 5 min at 4° C. The supernatant was removed and the pellet was dissolved in 150 µL cell lysis buffer. The samples were incubated on ice for 15 min. After that, the samples were stored at −80° C. until further processing.

2.4.1.1.3 Measurement of STAT1 Phosphorylation by ELISA

The Pathscan Phospho-STAT1 (Tyr701) Sandwich ELISA kit from Cell Signaling (Cat. no: #7234) was used to determine Phospho-STAT1 levels.

The cellular extracts were thawed on ice. The tubes were centrifuged for 5 min at 16,000 g, 4° C. and the cleared lysates were harvested. Meanwhile, the microwell strips from the kit were equilibrated to room temperature and wash buffer was prepared by diluting 20× wash buffer in $H_2O$, Samples were diluted 2-fold in sample diluent and 100 µL was added to the microwell strips. The strips were incubated overnight at 4° C.

The following day, the wells were washed 3 times with wash buffer. 100 µL of the detection antibody was added to the wells. The strips were incubated at 37° C. for 1 h. Then, the wells were washed 3 times with wash buffer again. 100 µL HRP-linked secondary antibody was added to each well and the samples were incubated at 37° C. After 30 min, the wells were washed 3 times again and 100 µL TMB substrate was added to all wells. When samples turned blue, 100 µL STOP solution was added to stop the reaction. Absorbance was measured at 450 nm.

2.4.1.2 Data Analysis

Inhibition of phosphoSTAT1 induction by IFNα in cell extracts was plotted against the compound concentration and $IC_{50}$ values were derived using Graphpad software. Data were retained if $R^2$ was larger than 0.8 and the hill slope was smaller than 3.

2.4.1.2 IL-8 ELISA

For GM-CSF stimulation, increase in interleukin-8 (IL-8) levels in plasma is measured using an IL-8 ELISA assay. Granulocyte macrophage-colony stimulating factor (GM-CSF)-induced interleukin 8 (IL-8) expression is a JAK2-mediated event. The IL-8 ELISA, which can be used to measure IL-8 levels in plasma samples, has been developed to assess the ability of a compound to inhibit JAK2-dependent signaling pathways.

Whole human blood, drawn from human volunteers who gave informed consent, is ex vivo treated with compound (1 h) and subsequently stimulated for 2 h with GM-CSF. The increase in IL-8 levels in plasma is measured using an IL-8 ELISA assay.

10 µg GM-CSF is dissolved in 100 µL $H_2O$ to obtain a 100 µg/mL stock solution. The stock solution is stored at −20° C.

A 3-fold dilution series of the test compound is prepared in DMSO (highest concentration: 10 mM). Subsequently, the compound is further diluted in medium (dilution factor dependent on desired final compound concentration).

2.4.1.2.1 Incubation of Blood with Compound and Stimulation with GM-CSF

Human blood is collected in heparinized tubes. The blood is divided in aliquots of 245 µL. Afterwards, 2.5 µL test compound dilution is added to each aliquot and the blood samples are incubated for 1 h at 37° C. The GM-CSF stock solution is diluted 100-fold in RPMI medium to obtain a 1 µg/mL work solution. 2.5 µL of the 1 µg/mL work solution is added to the blood samples (final concentration GM-CSF: 10 ng/mL). The samples are incubated at 37° C. for 2 h.

2.4.1.2.2 Preparation of Plasma Samples

The samples are centrifuged for 15 min at 1,000 g, 4° C. 100 µL of the plasma is harvested and stored at −80° C. until further use.

2.4.1.2.3 Measurement of IL-8 Levels by ELISA

The Human IL-8 Chemiluminescent Immunoassay kit from R&D Systems (Cat. no: Q8000B) is used to determine IL-8 levels.

Wash buffer is prepared by diluting 10× wash buffer in $H_2O$. Working glo reagent is prepared by adding 1 part Glo Reagent 1 to 2 parts Glo Reagent B 15 min to 4 h before use. 100 µL assay diluent RD1-86 is added to each well. After that, 50 µL of sample (plasma) is added. The ELISA plate is incubated for 2 h at room temperature, 500 rpm. All wells are washed 4 times with wash buffer and 200 µL IL-8 conjugate is added to each well. After incubation for 3 h at room temperature, the wells are washed 4 times with wash buffer and 100 µL working glo reagent is added to each well. The ELISA plate is incubated for 5 min at room temperature (protected from light). Luminescence is measured (0.5 s/well read time).

2.4.1.3 Results

For example, when submitted to this protocol, the $pIC_{50}$ of Compound 1 for inhibiting the INFα induced increase of pSTAT1 levels was 6.23±0.15 (SEM). This demonstrates that Compound 1 is potently inhibiting the JAK1 pathway in physiological setting.

2.4.2 IL-6 Stimulation Protocol

In addition, a flow cytometry analysis was performed to establish JAK1 over JAK2 compound selectivity ex vivo using human whole blood. Therefore, blood was taken from human volunteers who gave informed consent. Blood was then equilibrated for 30 minutes at 37° C. under gentle rocking, then aliquoted in Eppendorf tubes. Compound was added at different concentrations and incubated at 37° C. for 30 minutes under gentle rocking and subsequently stimulated for 20 minutes at 37° C. under gentle rocking with interleukin 6 (IL-6) for JAK1-dependent pathway stimulation or GM-CSF for JAK2-dependent pathway stimulation. Phospho-STAT1 and phospho-STAT5 were then evaluated using FACS analysis.

2.4.2.1 Phospho-STAT1 Assays

For IL-6-stimulated increase of Signal Transducers and Activators of Transcription 1 (pSTAT1) phosphorylation in white blood cell, human whole blood, drawn from human volunteers who gave informed consent, was ex vivo treated with the compound for 30 min and subsequently stimulated for 20 minutes with IL-6. The increase in phosphorylation of STAT1 by IL-6 in lymphocytes was measured using anti phospho-STAT1 antibody by FACS.

The 5× Lyse/Fix buffer (BD PhosFlow, Cat. No 558049) was diluted 5-fold with distilled water and pre-warmed at 37° C. The remaining diluted Lyse/Fix buffer was discarded.

10 μg rhIL-6 (R&D Systems, Cat No 206-IL) was dissolved in 1 ml of PBS 0.1% BSA to obtain a 10 μg/ml stock solution. The stock solution was aliquoted and stored at −80° C.

A 3-fold dilution series of the compound was prepared in DMSO (10 mM stock solution). Control-treated samples received DMSO instead of compound. All samples were incubated with a 1% final DMSO concentration.

2.4.2.1.1 Incubation of Blood with Compound and Stimulation with IL-6

Human blood was collected in heparinized tubes. The blood was divided in aliquots of 148.5 μl. Then, 1.5 μl of the test compound dilution was added to each blood aliquot and the blood samples were incubated for 30 min at 37° C. under gentle rocking. IL-6 stock solution (1.5 μl) was d added to the blood samples (final concentration 10 ng/ml) and samples were incubated at 37° C. for 20 min under gentle rocking.

2.4.2.1.2 White Blood Cell Preparation and CD4 Labeling

At the end of the stimulation period, 3 ml of 1× pre-warmed Lyse/Fix buffer was immediately added to the blood samples, vortexed briefly and incubated for 15 min at 37° C. in a water bath in order to lyse red blood cells and fix leukocytes, then frozen at −80° C. until further use.

For the following steps, tubes were thawed at 37° C. for approximately 20 minutes and centrifuged for 5 min at 400×g at 4° C. The cell pellet was washed with 3 ml of cold 1×PBS, and after centrifugation the cell pellet was resuspended in 100 μl of PBS containing 3% BSA. FITC-conjugated anti-CD4 antibody or control FITC-conjugated isotype antibody were added and incubated for 20 min at room temperature, in the dark.

2.4.2.1.3 Cell Permeabilization and Labeling with Anti Phospho-STAT1 Antibody After washing cells with 1×PBS, the cell pellet was resuspended in 100 μl of ice-cold 1×PBS and 900 μl ice-cold 100% methanol was added. Cells were then incubated at 4° C. for 30 min for permeabilization.

Permeabilized cells were then washed with 1×PBS containing 3% BSA and finally resuspended in 80 μl of 1×PBX containing 3% BSA.

20 μL of PE mouse anti-STAT1 (pY701) or PE mouse IgG2aκ isotype control antibody (BD Biosciences, Cat. No 612564 and 559319, respectively) were added and mixed, then incubated for 30 min at 4° C., in the dark.

Cells are then washed once with 1×PBS and analyzed on a FACSCanto II flow cytometer (BD Biosciences).

2.4.2.1.4 Fluorescence Analysis on FACSCanto II 50,000 total events were counted and Phospho-STAT1 positive cells were measured after gating on CD4+ cells, in the lymphocyte gate. Data were analyzed using the FACSDiva software and the percentage inhibition of IL-6 stimulation calculated on the percentage of positive cells for phospho-STAT1 on CD4+ cells.

2.4.2.2 Phospho-STAT5 Assay

For GM-CSF-stimulated increase of Signal Transducers and Activators of Transcription 5 (pSTAT5) phosphorylation in white blood cell, human whole blood, drawn from human volunteers who gave informed consent, is ex vivo treated with compound for 30 min and subsequently stimulated for 20 minutes with GM-CSF. The increase in phosphorylation of STAT5 by GM-CSF in monocytes is measured using an anti phospho-STAT5 antibody by FACS.

The 5× Lyse/Fix buffer (BD PhosFlow, Cat. No 558049) is diluted 5-fold with distilled water and pre-warmed at 37° C. Remaining diluted Lyse/Fix buffer is discarded.

10 μg rhGM-CSF (AbCys S. A., Cat No P300-03) is dissolved in 100 μl of PBS 0.1% BSA to obtain a 100 μg/ml stock solution. The stock solution is stored aliquoted at −80° C.

A 3-fold dilution series of the compound is prepared in DMSO (10 mM stock solution). Control-treated samples receive DMSO without the test compound. All samples are incubated with a 1% final DMSO concentration.

2.4.2.2.1 Incubation of Blood with Compound and Stimulation with GM-CSF

Human blood is collected in heparinized tubes. The blood is divided in aliquots of 148.5 μl. Then, 1.5 μl of compound dilution is added to each aliquot and the blood samples are incubated for 30 min at 37° C. under gentle rocking. GM-CSF stock solution (1.5 μl) is added to the blood samples (final concentration 20 pg/ml) and samples are incubated at 37° C. for 20 min under gentle rocking.

2.4.2.2.2 White Blood Cell Preparation and CD14 Labeling

At the end of the stimulation period, 3 ml of 1× pre-warmed Lyse/Fix buffer is immediately added to the blood samples, vortexed briefly and incubated for 15 min at 37° C. in a water bath in order to lyse red blood cells and fix leukocytes, then frozen at −80° C. until further use.

For the following steps, tubes are thawed at 37° C. for approximately 20 minutes and centrifuged for 5 min at 400×g at 4° C. The cell pellet is washed with 3 ml of cold 1×PBS, and after centrifugation the cell pellet is resuspended in 100 μl of PBS containing 3% BSA. FITC mouse anti-CD14 antibody (BD Biosciences, Cat. No 345784) or control FITC mouse IgG2bκ isotype antibody (BD Biosciences, Cat. No 555057) are added and incubated for 20 min at room temperature, in the dark.

2.4.2.2.3 Cell Permeabilization and Labeling with Anti Phospho-STAT5 Antibody

After washing cells with 1×PBS, the cell pellet is resuspended in 100 µl of ice-cold 1×PBS and 900 µl of ice-cold 100% methanol is added. Cells are then incubated at 4° C. for 30 min for permeabilization.

Permeabilized cells are then washed with 1×PBS containing 3% BSA and finally resuspended in 80 µl of 1×PBX containing 3% BSA.

20 µL of PE mouse anti-STAT5 (pY694) or PE mouse IgG1κ isotype control antibody (BD Biosciences, Cat. No 612567 and 554680, respectively) are added, mixed then incubated for 30 min at 4° C., in the dark.

Cells are then washed once with 1×PBS and analyzed on a FACSCanto II flow cytometer (BD Biosciences).

2.4.2.2.4 Fluorescence Analysis on FACSCanto II 50,000 total events are counted and Phospho-STAT5 positive cells are measured after gating on CD14+ cells. Data are analyzed using the FACSDiva software and correspond to the percentage of inhibition of GM-CSF stimulation calculated on the percentage of positive cells for phosphor-STAT5 on CD14+ cells.

2.4.2.2 Results

When submitted to this protocol, the percentage of inhibition (PIN) obtained from the mean of 3 healthy volunteers was determined for each test compounds. For example, Compound 1 was tested and returned a $pIC_{50}=6.08$ in the inhibition of STAT1 phosphorylation.

Example 3

In Vivo Models

Example 3.1

CIA Model 3.1.1 Materials

Completed Freund's adjuvant (CFA) and incomplete Freund's adjuvant (IFA) were purchased from Difco. Bovine collagen type II (CII), lipopolysaccharide (LPS), and Enbrel was obtained from Chondrex (Isle d'Abeau, France); Sigma (P4252, L'Isle d'Abeau, France), Whyett (25 mg injectable syringe, France) Acros Organics (Palo Alto, Calif.), respectively. All other reagents used were of reagent grade and all solvents were of analytical grade.

3.1.2 Animals

Dark Agouti rats (male, 7-8 weeks old) were obtained from Harlan Laboratories (Maison-Alfort, France). Rats were kept on a 12 hr light/dark cycle (0700-1900). Temperature was maintained at 22° C., and food and water were provided ad libitum.

3.1.3 Collagen Induced Arthritis (CIA)

One day before the experiment, CII solution (2 mg/mL) was prepared with 0.05 M acetic acid and stored at 4° C. Just before the immunization, equal volumes of adjuvant (IFA) and CII were mixed by a homogenizer in a pre-cooled glass bottle in an ice water bath. Extra adjuvant and prolonged homogenization may be required if an emulsion is not formed. 0.2 mL of the emulsion was injected intradermally at the base of the tail of each rat on day 1, a second booster intradermal injection (CII solution at 2 mg/mL in CFA 0.1 mL saline) was performed on day 9. This immunization method was modified from published methods (Sims et al, 2004; Jou et al., 2005).

3.1.4 Study Design

The therapeutic effects of the compounds were tested in the rat CIA model. Rats were randomly divided into equal groups and each group contained 10 rats. All rats were immunized on day 1 and boosted on day 9. Therapeutic dosing lasted from day 16 to day 30. The negative control group was treated with vehicle (MC 0.5%) and the positive control group with Enbrel (10 mg/kg, 3× week., s.c.). A compound of interest was typically tested at 3 doses, e.g. 3, 10, 30 mg/kg, p.o.

3.1.5 Clinical Assessment of Arthritis

Arthritis is scored according to the method of Khachigian 2006, Lin et al 2007 and Nishida et al. 2004). The swelling of each of the four paws is ranked with the arthritic score as follows: 0—no symptoms; 1—mild, but definite redness and swelling of one type of joint such as the ankle or wrist, or apparent redness and swelling limited to individual digits, regardless of the number of affected digits; 2-moderate redness and swelling of two or more types of joints; 3-severe redness and swelling of the entire paw including digits; 4-maximally inflamed limb with involvement of multiple joints (maximum cumulative clinical arthritis score 16 per animal) (Nishida et al., 2004).

To permit the meta-analysis of multiple studies the clinical score values were normalised as follows:

AUC of clinical score (AUC score): The area under the curve (AUC) from day 1 to day 14 was calculated for each individual rat. The AUC of each animal was divided by the average AUC obtained for the vehicle in the study from which the data on that animal was obtained and multiplied by 100 (i.e. the AUC was expressed as a percentage of the average vehicle AUC per study).

Clinical score increase from day 1 to day 14 (End point score): The clinical score difference for each animal was divided by the average clinical score difference obtained for the vehicle in the study from which the data on that animal was obtained and multiplied by 100 (i.e. the difference was expressed as a percentage of the average clinical score difference for the vehicle per study).

3.1.6 Change in Body Weight (%) after Onset of Arthritis

Clinically, body weight loss is associated with arthritis (Shelton et al., 2005; Argiles et al., 1998; Rall, 2004; Walsmith et al., 2004). Hence, changes in body weight after onset of arthritis can be used as a non-specific endpoint to evaluate the effect of therapeutics in the rat model. The change in body weight (%) after onset of arthritis was calculated as follows:

$$\text{Mice:} \frac{\text{Body Weight}_{(week6)} - \text{Body Weight}_{(week5)}}{\text{Body Weight}_{(week\ 5)}} \times 100\%$$

$$\text{Rats:} \frac{\text{Body Weight}_{(week4)} - \text{Body Weight}_{(week3)}}{\text{Body Weight}_{(week3)}} \times 100\%$$

3.1.7 Radiology

X-ray photos were taken of the hind paws of each individual animal. A random blind identity number was assigned to each of the photos, and the severity of bone erosion was ranked by two independent scorers with the radiological Larsen's score system as follows: 0—normal with intact bony outlines and normal joint space; 1—slight abnormality with any one or two of the exterior metatarsal bones showing slight bone erosion; 2—definite early abnormality with any three to five of the exterior metatarsal bones showing bone erosion; 3—medium destructive abnormality with all the exterior metatarsal bones as well as any one or two of the interior metatarsal bones showing definite bone erosions; 4—severe destructive abnormality with all the metatarsal bones showing definite bone erosion and at least one of the inner metatarsal joints completely eroded leaving some bony joint outlines partly preserved; 5-mutilating abnormality without bony outlines. This scoring system is a modification from Salvemini et al., 2001; Bush et al., 2002; Sims et al., 2004; Jou et al., 2005.

3.1.8 Histology

After radiological analysis, the hind paws of mice were fixed in 10% phosphate-buffered formalin (pH 7.4), decalcified with rapid bone decalcifiant for fine histology (Laboratories Eurobio) and embedded in paraffin. To ensure extensive evaluation of the arthritic joints, at least four serial sections (5 μm thick) were cut and each series of sections were 100 μm in between. The sections were stained with hematoxylin and eosin (H&E). Histologic examinations for synovial inflammation and bone and cartilage damage were performed double blind. In each paw, four parameters were assessed using a four-point scale. The parameters were cell infiltration, pannus severity, cartilage erosion and bone erosion. Scoring was performed according as follows: 1-normal, 2-mild, 3-moderate, 4-marked. These four scores are summed together and represented as an additional score, namely the 'RA total score'.

3.1.9 Micro-Computed Tomography (KT) Analysis of Calcaneus (Heel Bone):

Bone degradation observed in RA occurs especially at the cortical bone and can be revealed by μECT analysis (Sims N A et al., Arthritis Rheum. 50 (2004) 2338-2346: Targeting osteoclasts with zoledronic acid prevents bone destruction in collagen-induced arthritis; Oste L et al., ECTC Montreal 2007: A high throughput method of measuring bone architectural disturbance in a murine CIA model by micro-CT morphometry). After scanning and 3D volume reconstruction of the calcaneus bone, bone degradation is measured as the number of discrete objects present per slide, isolated in silico perpendicular to the longitudinal axis of the bone. The more the bone is degraded, the more discrete objects are measured. 1000 slices, evenly distributed along the calcaneus (spaced by about 10.8 μm), are analyzed.

3.1.10 Steady State PK

At day 7 or 11, blood samples were collected at the retro-orbital sinus with lithium heparin as anti-coagulant at the following time points: predose, 1, 3 and 6 hrs. Whole blood samples were centrifuged and the resulting plasma samples were stored at −20° C. pending analysis. Plasma concentrations of each test compound were determined by an LC-MS/MS method in which the mass spectrometer was operated in positive electrospray mode. Pharmacokinetic parameters were calculated using Winnonlin® (Pharsight®, United States) and it was assumed that the predose plasma levels were equal to the 24 hrs plasma levels.

Table V below summarises the results obtained for several PK parameters, for the compound of the invention and a comparative example, illustrating the improved PK properties (e.g. Cmax, T1/2) of the compound of the invention.

TABLE V

| | | Compound 1 PO (mg/kg/day) | | | | | | Compound 2 PO (mg/kg/day) | |
|---|---|---|---|---|---|---|---|---|---|
| | | 0.1 | 0.3 | 1 | 3 | 10 | 30 | 10 | 30 |
| Cmax | (ng/mL) | 5.18 | 19.3 | 102 | 363 | 1,167 | 3,805 | 867 | 2630 |
| Tmax | (h) | 3 | 1 | 1 | 1 | 1 | 1 | 1 | 1 |
| AUC(0-24 h) | (ng.h/mL) | 30 | 163 | 931 | 1,932 | 7,172 | 27,767 | 2019 | 7809 |
| T1/2 | (h) | NC | NC | 3.6 | 5.6 | 4.5 | 3.9 | 1.17 | 3.36 |

3.1.11 Results

Table VI below summarises the results obtained for compounds 1 and 2 in the rat CIA model, a "*" indicates that there was a statistically significant improvement in the score, p 0.05 vs. untreated control.

TABLE VI

| | Dose | Clinical Assessment$ | | | |
|---|---|---|---|---|---|
| Compound | (mg/kg/day) | End point score | AUC Score | Paw swelling | Larsen' Score |
| Compound 1 | 0.1 | * | * | | |
| | 0.3 | * | * | * | |
| | 1 | * | * | * | |
| | 3 | * | * | * | * |
| Compound 2 | 10 | * | | | |
| | 30 | * | | * | * |

$"Clinical Score" refers to the normalized AUC score/normalized end point score obtained for Compound 1, and the AUC score/end point score for Compound 2.

Compound 1 exhibited statistically significant improvements in the normalized clinical score values (calculated as AUC or as the difference from day 1 to day 14) at a dose of 0.1 mg/kg. Additionally, a statistically significant increase in the paw swelling readout and in the Larsen score were seen at doses of 0.3 mg/kg and 3 mg/kg respectively. In contrast, Compound 2 exhibited statistically significant improvements only in the normalized clinical score values (on day 14) at a dose of 10 mg/kg. Additionally, a statistically significant increase in the paw swelling readout and in the Larsen score were seen at doses of 30 mg/kg. Therefore, Compound 1 shows a 100 fold improvement in efficacy over Compound 2 when the oral doses are compared. In particular, at a dose of 3 mg/kg for Compound 1, statistically significant improvements were seen in all measures, however, a higher dose of Compound 2 resulted in only a statistically significant improvement in the clinical score. This improvement in in vivo potency cannot be attributed to increased exposure of the compound as it can be see that the AUC(0-24 h) is lower for Compound 1 at 0.1, 0.3 and 1 mg/kg/day compared to Compound 2 at 10 mg/kg/day.

Example 3.2

Septic Shock Model

Injection of lipopolysaccharide (LPS) induces a rapid release of soluble tumour necrosis factor (TNF-alpha) into the periphery. This model was used to analyse prospective blockers of TNF release in vivo.

Six BALB/cJ female mice (20 g) per group were treated at the intended dosing once, po. Thirty minutes later, LPS (15 µg/kg; E. Coli serotype 0111:B4) was injected ip. Ninety minutes later, mice were euthanized and blood was collected. Circulating TNF alpha levels were determined using commercially available ELISA kits. Dexamethasone (5 µg/kg) was used as a reference anti-inflammatory compound. Selected compounds were tested at one or multiple doses, e.g. 3 and/or 10 and/or 30 mg/kg, po.

Compounds 1, 2 and 10 were active at a dose of 30 mg/kg, po.

Example 3.3

MAB Model

The MAB model allows a rapid assessment of the modulation of an RA-like inflammatory response by therapeutics (Kachigian L M. Nature Protocols (2006) 2512-2516: Collagen antibody-induced arthritis). DBA/J mice are injected i.v. with a cocktail of mAbs directed against collagen II. One day later, compound treatment is initiated (vehicle: 10% (v/v) HPβCD). Three days later, mice receive an i.p. LPS injection (50 µg/mouse), resulting in a fast onset of inflammation. Compound treatment is continued until 10 days after the mAb injection. Inflammation is read by measuring paw swelling and recording the clinical score of each paw. The cumulative clinical arthritis score of four limbs is presented to show the severity of inflammation. A scoring system is applied to each limb using a scale of 0-4, with 4 being the most severe inflammation.

0 Symptom free
1 Mild, but definite redness and swelling of one type of joint such as the ankle or wrist, or apparent redness and swelling limited to individual digits, regardless of the number of affected digits
2 Moderate redness and swelling of two or more types of joints
3 Severe redness and swelling of the entire paw including digits
4 Maximally inflamed limb with involvement of multiple joints Example 3.4

Oncology Models

In vivo models to validate efficacy of small molecules towards JAK2-driven myeloproliferative diseases are described by Wernig et al. Cancer Cell 13, 311, 2008 and Geron et al. Cancer Cell 13, 321, 2008.

Example 3.5

Mouse IBD Model

In vitro and in vivo models to validate efficacy of small molecules towards IBD are described by Wirtz et al. 2007.

Example 3.6

Mouse Asthma Model

In vitro and in vivo models to validate efficacy of small molecules towards asthma are described by Nials et al., 2008; Ip et al. 2006; Pernis et al., 2002; Kudlacz et al., 2008.

Example 4

Pharmacokinetic, DMPK and Toxicity Assays

Example 4.1

Thermodynamic Solubility

A solution of 1 mg/mL of the test compound is prepared in a 0.2M phosphate buffer pH 7.4 or a 0.1M citrate buffer pH 3.0 at room temperature in a glass vial.

The samples are rotated in a Rotator drive STR 4 (Stuart Scientific, Bibby) at speed 3.0 at room temperature for 24 hrs.

After 24 hrs, 800 µL of the sample is transferred to an eppendorf tube and centrifuged 5 min at 14000 rpm. 200 µL of the supernatant of the sample is then transferred to a MultiscreenR Solubility Plate (Millipore, MSSLBPC50) and the supernatant is filtered (10-12" Hg) with the aid of a vacuum manifold into a clean Greiner polypropylene V-bottom 96 well plate (Cat no. 651201). 5 µL of the filtrate is diluted into 95 µL (F20) of the same buffer used to incubate in the plate containing the standard curve (Greiner, Cat no. 651201).

The standard curve for the compound is prepared freshly in DMSO starting from a 10 mM DMSO stock solution diluted factor 2 in DMSO (5000 µM) and then further diluted in DMSO up to 19.5 µM. 3 µl of the dilution series as from 5000 µM is then transferred to a 97 µL acetonitrile-buffer mixture (50/50). The final concentration range was 2.5 to 150 µM.

The plate is sealed with sealing mats (MA96RD-045, www.kinesis.co.uk) and samples are measured at room temperature on LCMS (ZQ 1525 from Waters) under optimized conditions using Quanoptimize to determine the appropriate mass of the molecule.

The samples are analyzed on LCMS with a flow rate of 1 mL/min. Solvent A is 15 mM ammonia and solvent B is acetonitrile. The sample is run under positive ion spray on an XBridge C18 3.5 μM (2.1×30 mm) column, from Waters. The solvent gradient has a total run time of 2 minutes and ranges from 5% B to 95% B.

Peak areas are analyzed with the aid of Masslynx software package and peak areas of the samples are plotted against the standard curve to obtain the solubility of the compound.

Solubility values are reported in μM or μg/mL.

Example 4.2

Aqueous Solubility

Starting from a 10 mM stock in DMSO, a serial dilution of the compound was prepared in DMSO. The dilution series was transferred to a 96 NUNC Maxisorb plate F-bottom (Cat no. 442-404) and 0.2M phosphate buffer pH7.4 or 0.1M citrate buffer pH 3.0 at room temperature was added.

The final concentration ranged from 200 μM to 2.5 μM in 5 equal dilution steps. The final DMSO concentration did not exceed 2%. 200 μM Pyrene was added to the corner points of each 96 well plate and served as a reference point for calibration of Z-axis on the microscope.

The assay plates were sealed and incubated for 1 hr at 37° C. while shaking at 230 rpm. The plates were then scanned under a white light microscope, yielding individual pictures of the precipitate per concentration. The precipitate was analyzed and converted into a number which was plotted onto a graph. The first concentration at which the compound appears completely dissolved is the concentration is reported below, however the true concentration lies somewhere between this concentration and one dilution step higher.

Solubility values are reported in μg/mL

TABLE VII

| Compound # | pH 3.0 (μg/mL) | pH 7.4 (μg/mL) |
|---|---|---|
| 1 | >85 | >85 |
| 2 | >38 | >38 |
| 10 | >87.9 | >87.9 |

Example 4.3

Plasma Protein Binding (Equilibrium Dialysis)

A 10 mM stock solution of the compound in DMSO was diluted with a factor 5 in DMSO. This solution was further diluted in freshly thawed human, rat, mouse or dog plasma (BioReclamation INC) with a final concentration of 10 μM and final DMSO concentration of 0.5% (5.5 μL in 1094.5 μL plasma in a PP-Masterblock 96 well (Greiner, Cat no. 780285))

A Pierce Red Device plate with inserts (ThermoScientific, Cat no. 89809) was prepared and filled with 750 μL PBS in the buffer chamber and 500 μL of the spiked plasma in the plasma chamber. The plate was incubated for 4 hrs at 37° C. while shaking at 230 rpm. After incubation, 120 μL of both chambers was transferred to 360 μL acetonitrile in a 96-well round bottom, PP deep-well plates (Nunc, Cat no. 278743) and sealed with an aluminum foil lid. The samples were mixed and placed on ice for 30 min. This plate was then centrifuged 30 min at 1200 rcf at 4° C. and the supernatant was transferred to a 96 v-bottom PP plate (Greiner, 651201) for analysis on LCMS.

The plate is sealed with sealing mats (MA96RD-04S) of www.kinesis.co.uk and samples are measured at room temperature on LCMS (ZQ 1525 from Waters) under optimized conditions using Quanoptimize to determine the appropriate mass of the molecule.

The samples were analyzed on LCMS with a flow rate of 1 ml/min. Solvent A was 15 mM ammonia and solvent B was acetonitrile. The sample was run under positive ion spray on an XBridge C18 3.5 μM (2.1×30 mm) column, from Waters. The solvent gradient has a total run time of 2 minutes and ranges from 5% B to 95% B.

Peak area from the compound in the buffer chamber and the plasma chamber are considered to be 100% compound. The percentage bound to plasma was derived from these results and was reported as percentage bound to plasma.

The solubility of the compound in the final test concentration in PBS was inspected by microscope to indicate whether precipitation is observed or not.

TABLE VIII

| Compound # | Human (%) | Rat (%) |
|---|---|---|
| 1 | 76.4 | 65.7 |
| 2 | 70.5 | 64.5 |
| 10 | n/a | 51 |
| 11 | 91.25 | 76.5 |

Example 4.4

Microsomal Stability

A 10 mM stock solution of compound in DMSO was diluted 1000 fold in a 182 mM phosphate buffer pH7.4 in a 96 deep well plate (Greiner, Cat no. 780285) and pre-incubated at 37° C.

40 μL of deionised water was added to a well of a polypropylene Matrix 2D barcode labelled storage tube (Thermo Scientific) and pre-incubated at 37° C.

A Glucose-6-phophate-dehydrogenase (G6PDH) working stock solution was prepared in 182 mM phosphate buffer pH7.4 and placed on ice before use. A co-factor containing $MgCl_2$, glucose-6-phosphate and NADP+ was prepared in deionised water and placed on ice before use.

A final working solution containing liver microsomes (Xenotech) of a species of interest (human, mouse, rat, dog), previously described G6PDH and co-factors was prepared and this mix was incubated for no longer than 20 minutes at room temperature.

30 μL of the pre-heated compound dilution was added to 40 μL of pre-heated water in the Matrix tubes and 30 μL of the microsomal mix was added. Final reaction concentrations were 3 μM compound, 1 mg microsomes, 0.4 U/mL GDPDH, 3.3 mM $MgCl_2$, 3.3 mM glucose-6-phosphate and 1.3 mM NADP+.

To measure percentage remaining of compound at time zero MeOH or ACN was added (1:1) to the well before adding the microsomal mix. The plates were sealed with Matrix Sepra Seals™ (Matrix, Cat. No. 4464) and shaken for a few seconds ensure complete mixing of all components.

The samples which were not stopped are incubated at 37° C., 300 rpm and after 1 hr of incubation the reaction was stopped with MeOH or ACN (1:1).

After stopping the reaction the samples were mixed and placed on ice for 30 min to precipitate the proteins. The plates were then centrifuged 30 min at 1200 rcf at 4° C. and the supernatant was transferred to a 96 v-bottom PP plate (Greiner, 651201) for analysis on LCMS.

These plates were sealed with sealing mats (MA96RD-04S) of www.kinesis.co.uk and samples were measured at room temperature on LCMS (ZQ 1525 from Waters) under optimized conditions using Quanoptimize to determine the appropriate mass of the parent molecule.

The samples were analyzed on LCMS with a flow rate of 1 mL/min. Solvent A was 15 mM ammonia and solvent B was methanol or acetonitrile, depending on the stop solution used. The samples were run under positive ion spray on an XBridge C18 3.5 μM (2.1×30 mm) column, from Waters. The solvent gradient had a total run time of 2 minutes and ranges from 5% B to 95% B.

Peak area from the parent compound at time 0 was considered to be 100% remaining. The percentage remaining after 1 hr incubation was calculated from time 0 and was calculated as the percentage remaining. The solubility of the compound in the final test concentration in buffer is inspected by microscope and results are reported.

The data on microsomal stability are expressed as a percentage of the total amount of compound remaining after 60 min.

TABLE IX

| Compound # | Human (%) | Rat (%) |
| --- | --- | --- |
| 1 | 87.2 | 65.6 |
| 2 | 73 | 38 |
| 10 | 102 | 89 |
| 11 | 51 | 26 |

Example 4.5

Caco2 Permeability

Bi-directional Caco-2 assays were performed as described below. Caco-2 cells were obtained from European Collection of Cell Cultures (ECACC, cat 86010202) and used after a 21 day cell culture in 24-well Transwell plates (Fisher TKT-545-020B).

$2 \times 10^5$ cells/well were seeded in plating medium consisting of DMEM+GlutaMAXI+1% NEAA+10% FBS (FetalClone II)+1% Pen/Strep. The medium was changed every 2-3 days. Test and reference compounds (propranolol and rhodamine123 or vinblastine, all purchased from Sigma) were prepared in Hanks' Balanced Salt Solution containing 25 mM HEPES (pH7.4) and added to either the apical (125 μL) or basolateral (600 μL) chambers of the Transwell plate assembly at a concentration of 10 μM with a final DMSO concentration of 0.25%.

50 μM Lucifer Yellow (Sigma) was added to the donor buffer in all wells to assess integrity of the cell layers by monitoring Lucifer Yellow permeation. As Lucifer Yellow (LY) cannot freely permeate lipophilic barriers, a high degree of LY transport indicates poor integrity of the cell layer.

After a 1 hr incubation at 37° C. while shaking at an orbital shaker at 150 rpm, 70 μL aliquots were taken from both apical (A) and basal (B) chambers and added to 100 μL1 50:50 acetonitrile:water solution containing analytical internal standard (0.5 μM carbamazepine) in a 96 well plate.

Lucifer yellow was measured with a Spectramax Gemini XS (Ex 426 nm and Em 538 nm) in a clean 96 well plate containing 150 μL of liquid from basolateral and apical side.

Concentrations of compound in the samples were measured by high performance liquid-chromatography/mass spectroscopy (LC-MS/MS).

Apparent permeability ($P_{app}$) values were calculated from the relationship:

$$P_{app} = [\text{compound}]_{acceptor\,final} \times V_{acceptor} ([\text{compound}]_{donor\,initial} \times V_{donor})/T_{inc} \times V_{donor}/\text{surface area} \times 60 \times 10^{-6} \text{ cm/s}$$

V=chamber volume
$T_{inc}$=incubation time.
Surface area=0.33 cm²

The Efflux ratios, as an indication of active efflux from the apical cell surface, were calculated using the ratio of $P_{app}$ B>A/$P_{app}$ A>B.

The following assay acceptance criteria were used:
Propranolol: $P_{app}$ (A>B) value>20(×10⁻⁶ cm/s)
Rhodamine 123 or Vinblastine: $P_{app}$ (A>B) value<5 (×10⁻⁶ cm/s) with Efflux ratio≧5.
Lucifer yellow permeability: ≦100 nm/s

TABLE X

| Compound # | $P_{app}$ A > B (×10−6 cm/sec) | Efflux ratio |
| --- | --- | --- |
| 1 | 3.33 | 15.7 |
| 2 | 25 | 0.95 |
| 10 | 0.05 | 97.6 |
| 11 | 36.5 | 0.9 |

Example 4.6

Pharmacokinetic Study in Rodents 4.6.1 Animals

Sprague-Dawley rats (male, 5-6 weeks old) were obtained from Janvier (France). Rats were acclimatized for at least 7 days before treatment and were kept on a 12 hr light/dark cycle (0700-1900). Temperature was maintained at approximately 22° C., and food and water were provided ad libitum. Two days before administration of compounds 1 and 2, rats underwent surgery to place a catheter in the jugular vein under isoflurane anesthesia. After the surgery, rats were housed individually. Rats were deprived of food for at least 16 hours before oral dosing and 6 hours after. Water was provided ad libitum.

4.6.2 Pharmacokinetic Study

Compounds were formulated in PEG200/physiological saline (60/40) for the intravenous route and in 0.5% methylcellulose (compounds 1 and 2) and 10% hydroxylpropyl-β-cyclodextrine pH3 (compound 11) for the oral route. Test compounds were orally dosed as a single esophageal gavage at 5 mg/kg under a dosing volume of 5 ml/kg and intravenously dosed as a bolus via the caudal vein at 1 mg/kg under a dosing volume of 5 mL/kg. Each group consisted of 3 rats. For compounds 1 and 2 blood samples were collected via the jugular vein with lithium heparin as anti-coagulant at the following time points: 0.05, 0.25, 0.5, 1, 3, 5 and 8 hrs (intravenous route), and 0.25, 0.5, 1, 3, 5, 8 and 24 hrs (oral route). For compound 11, blood samples were collected at the retro-orbital sinus with lithium heparin as anti-coagulant at the following time points 0.25, 1, 3 and 6 hrs (oral route). Whole blood samples were centrifuged at 5000 rpm for 10 min and the resulting plasma samples were stored at −20° C. pending analysis.

4.6.3 Quantification of Compound Levels in Plasma

Plasma concentrations of each test compound were determined by an LC-MS/MS method in which the mass spectrometer was operated in positive electrospray mode.

4.6.4 Determination of Pharmacokinetic Parameters

Pharmacokinetic parameters were calculated using Winnonlin® (Pharsight®, United States).

TABLE XI

| | Compound 1 | | Compound 2 | | Compound 11 |
|---|---|---|---|---|---|
| | IV 1 mg/kg (n = 3) | PO 5 mg/kg (n = 3) | IV 1 mg/kg (n = 3) | PO 5 mg/kg (n = 3) | PO 5 mg/kg (n = 3) |
| C0 or Cmax (ng/mL) | 1407 (28) | 310 (33) | 863 (4) | 1320 (42) | 547 (8) |
| Tmax (h) | | 2.2 [0.5-5] | | 0.33 [0.25-0.5] | 0.25 [0.25-0.25] |
| AUC(0-z) (ng.h/mL) | 722 (2) | 1429 (24) | 470 (5) | 1437 (33) | 690 (23) |
| AUC (0-24 h) (ng.h/mL) | 739 (2) | 1681 (8) | 474 (5) | 1465 (30) | |
| Cl | 1.35 (2) | | 2.12 (5) | | |
| Vss | 1.76 (3) | | 1.46 (4) | | |
| T1/2 | 1.6 (3) | | 0.74 (8) | 0.92 (57) | 0.92 (7) |
| F (%) | | 45 | | 62 | |

Example 4.7

7-Day Rat Toxicity Study

A 7-day oral toxicity study with test compounds is performed in Sprague-Dawley male rats to assess their toxic potential and toxicokinetics, at daily doses of 100, 300 and 500 mg/kg/day, by gavage, at the constant dosage-volume of 5 mL/kg/day.

The test compounds are formulated in 30% (v/v) HPβCD in purified water. Each group included 5 principal male rats as well as 3 satellite animals for toxicokinetics. A fourth group is given 30% (v/v) HPβCD in water only, at the same frequency, dosage volume and by the same route of administration, and acted as the vehicle control group.

The goal of the study is to determine the lowest dose that resulted in no adverse events being identified (no observable adverse effect level—NOAEL).

Example 4.8

Hepatocyte Stability

Models to evaluate metabolic clearance in hepatocyte are described by McGinnity et al. Drug Metabolism and Disposition 2008, 32, 11, 1247.

Example 4.9

Liability for QT Prolongation

Potential for QT prolongation was assessed in the hERG patch clamp assay.
Conventional Whole-Cell Patch-Clamp
Whole-cell patch-clamp recordings were performed using an EPC10 amplifier controlled by Pulse v8.77 software (HEKA). Series resistance was typically less than 10 MΩ and compensated by greater than 60%, recordings were not leak subtracted. Electrodes were manufactured from GC150TF pipette glass (Harvard).

The external bathing solution contained: 135 mM NaCl, 5 mM KCl, 1.8 mM $CaCl_2$, 5 mM Glucose, 10 mM HEPES, pH 7.4.

The internal patch pipette solution contained: 100 mM Kgluconate, 20 mM KCl, 1 mM $CaCl_2$, 1 mM $MgCl_2$, 5 mM $Na_2ATP$, 2 mM Glutathione, 11 mM EGTA, 10 mM HEPES, pH 7.2.

Drugs were perfused using a Biologic MEV-9/EVH-9 rapid perfusion system.

All recordings were performed on HEK293 cells stably expressing hERG channels. Cells are cultured on 12 mm round coverslips (German glass, Bellco) anchored in the recording chamber using two platinum rods (Goodfellow). hERG currents were evoked using an activating pulse to +40 mV for 1000 ms followed by a tail current pulse to −50 mV for 2000 ms, holding potential was −80 mV. Pulses were applied every 20 s and all experiments were performed at room temperature.
Results For example, when subjected to this assay, the measured $IC_{50}$ of Compound 1 was greater than 150 μM.

GENERAL CONCLUSIONS

The data provided in the present application demonstrate that Compound 1 (the compound of the invention) exhibits significantly improved in vivo potency compared to structurally similar compounds. This improvement is unexpected and could not have been predicted by a person of skill in the art, particularly because many of these structurally similar compounds exhibit very similar in vitro potency against JAK1 and JAK2.

It will be appreciated by those skilled in the art that the foregoing descriptions are exemplary and explanatory in nature, and intended to illustrate the invention and its preferred embodiments. Through routine experimentation, an artisan will recognise apparent modifications and variations that may be made without departing from the spirit of the invention. Thus, the invention is intended to be defined not by the above description, but by the following claims and their equivalents.

REFERENCES

Choy E H, Panayi G S. (2001). N Engl J Med. 344: 907-16.
Chubinskaya S and Kuettner K E (2003). Regulation of osteogenic proteins by chondrocytes. The international journal of biochemistry & cell biology 35(9)1323-1340.
Clegg D O et al. (2006) N Engl J Med. 2006 354:795-808. Glucosamine, chondroitin sulfate, and the two in combination for painful knee osteoarthritis.
Firestein G S. (2003). Nature. 423:356-61.
Lee D M, Weinblatt M E (2001). Lancet. 358: 903-11.
Legendre F, Dudhia J, Pujol J-P, Bogdanowicz P. (2003) JAK/STAT but not ERK1/ERK2 pathway mediates interleuking (IL)-6/soluble IL-6R down-regulation of type II collagen, aggrecan core, and link protein transcription in articular chondrocytes. J Biol Chem. 278(5)2903-2912.

Li W Q, Dehnade F, Zafarullah M. (2001) Oncostatin M-induced matrix metalloproteinase and tissue inhibitor of metalloproteinase-3 genes expression in chondrocytes requires janus kinase/STAT signaling pathway. (2001) J Immunol 166:3491-3498.

O'Dell J R. (2004) Therapeutic strategies for rheumatoid arthritis. N Engl J Med. 350(25):2591-602.

Osaki M, Tan L, Choy B K, Yoshida Y, Cheah K S E, Auron P E, Goldring M B. (2003) The TATA-containing core promoter of the type II collagen gene (COL2A1) is the target of interferon-gamma-mediated inhibition in human chondrocytes: requirement for STAT1alpha, JAK1 and JAK2. Biochem J 369:103-115.

Otero M, Lago R, Lago F, Gomez Reino J J, Gualillo O. (2005) Signalling pathway involved in nitric oxide synthase type II activation in chondrocytes: synergistic effect of leptin with interleukin-1. Arthritis Research & Therapy 7:R581-R591.

Sims N A et al., (2004) Targeting osteoclasts with zoledronic acid prevents bone destruction in collagen-induced arthritis, Arthritis Rheum. 50 2338-2346:

Rodig S J, Meraz M A, White J M, Lampe P A, Riley J K, Arthur C D, King K L, Sheehan K C F, Yin L, Pennica D, Johnson E M, Schreiber R D. (1998) Disruption of the Jak1 gene demonstrates obligatory and nonredundant roles of the jaks in cytokine-induced biologic responses Cell 93: 373-383.

Smolen J S, Steiner G. (2003). Nat Rev Drug Discov. 2: 473-88.

Wieland H A, Michaelis M, Kirschbaum B J, Rudolphi K A. (2005). Nat Rev Drug Discov. 4:331-44. Osteoarthritis—an untreatable disease?

Tam, L., McGlynn, L. M., Traynor, P., Mukherjee, R., Bartlett, J. M. S., Edwards, J. (2007) British Journal of Cancer, 97, 378-383

Constantinescu et al., 2007, Trends in Biochemical Sciences 33(3): 122-131

Tetsuji Naka, Norihiro Nishimoto and Tadamitsu Kishimoto, Arthritis Res 2002, 4 (suppl 3):5233-5242

O'Shea J. et al. Nature Review Drug Discovery 3 (2004) 555-564: A new modality for immunesupresion: targeting the JAK/STAT pathway Vainchenker W. et al. Seminars in Cell & Developmental Biology 19 (2008) 385-393: JAKs in pathology: Role of Janus kinases in hematopoietic malignancies and immune deficiencies Levy D. and Loomis C. New England Journal of Medicine 357 (2007) 1655-1658: STAT3 signaling and the Hyper-IgE-syndrome Wernig et al. (2008) Efficacy of TG101348, a selective JAK2 inhibitor, in treatment of a murine model of JAK2V617F-induced polycythemia vera, Cancer Cell 13(4), 311-320

Geron et al. (2008) Selective inhibition of JAK2-driven erythroid differentiation of polycythemia vera progenitors Cancer Cell 13 (4), 321-30

Wirtz et al. (2007) Mouse Models of Inflammatory Bowel Disease, Advanced Drug Delivery Reviews, 2007, 1073-1083:

Nials et al. (2008) Mouse Models of Allergic Asthma: Acute and Chronic Allergen Challenge, Disease Models & Mechanisms, 213-220.

Ip et al. (2006) Interleukin (IL)-4 and IL-13 up-regulate monocyte chemoattractant protein-1 expression in human bronchial epithelial cells: involvement of p38 mitogen-activated protein kinase, extracellular signal-regulated kinase 1/2 and Janus kinase-2 but not c-Jun NH2-terminal kinase 1/2 signalling pathways, Clin. Exp. Immun, 162-172.

Pernis et al. (2002) JAK-STAT signaling in asthma J. Clin. Invest. 1279.

Kudlacz et al. (2008) The JAK-3 inhibitor CP-690550 is a potent anti-inflammatory agent in a murine model of pulmonary eosinophilia, Eur J Pharmaco 154-161.

Mullighan C G, Zhang J, Harvey R C, Collins-Underwood J R, Schulman B A, Phillips L A, Tasian S K, Loh M L, Su X, Liu W, Devidas M, Atlas S R, Chen I-M, Clifford R J, Gerhard D S, Carroll W L, Reaman G H, Smith M, Downing J R, Hunger S P Willmane C L; (2009) JAK mutations in high-risk childhood acute lymphoblastic leukemia, PNAS May 22. [Epub ahead of print]

Argiles J M, Lopez-Soriano F J. (1998) Catabolic proinflammatory cytokines. Curr Opin Clin Nutr Metab Care. 1:245-51.

Bush K A, Farmer K M, Walker J S, Kirkham B W. (2002) Reduction of joint inflammation and bone erosion in rat adjuvant arthritis by treatment with interleukin-17 receptor IgG1 Fc fusion protein. Arthritis Rheum. 46: 802-5.

Jou I M, Shiau A L, Chen S Y, Wang C R, Shieh D B, Tsai C S, Wu C L. (2005) Thrombospondin 1 as an effective gene therapeutic strategy in collagen-induced arthritis. Arthritis Rheum. 52:339-44.

Nishida K, Komiyama T, Miyazawa S, Shen Z N, Furumatsu T, Doi H, Yoshida A, Yamana J, Yamamura M, Ninomiya Y, Inoue H, Asahara H. (2004) Histone deacetylase inhibitor suppression of autoantibody-mediated arthritis in mice via regulation of p16INK4a and p21(WAF1/Cip1) expression. Arthritis Rheum. 10: 3365-76.

Rall L C, Roubenoff R. (2004) Rheumatoid cachexia: metabolic abnormalities, mechanisms and interventions. Rheumatology; 10:1219-23.

Salvemini D, Mazzon E, Dugo L, Serraino I, De Sarro A, Caputi A P, Cuzzocrea S. (2001) Amelioration of joint disease in a rat model of collagen-induced arthritis by M40403, a superoxide dismutase mimetic. Arthritis Rheum. 44:2909-21.

Shelton D L, Zeller J, Ho W H, Pons J, Rosenthal A. (2005) Nerve growth factor mediates hyperalgesia and cachexia in auto-immune arthritis. Pain. 116:8-16.

Sims N A, Green J R, Glatt M, Schlict S, Martin T J, Gillespie M T, Romas E. (2004) Targeting osteoclasts with zoledronic acid prevents bone destruction in collagen-induced arthritis. Arthritis Rheum., 50: 2338-46.

Walsmith J, Abad L, Kehayias J, Roubenoff R. (2004) Tumor necrosis factor-alpha production is associated with less body cell mass in women with rheumatoid arthritis. J Rheumatol.; 31:23-9.

Khachigian, L. M. Collagen antibody-induced arthritis. (2006) Nature Protocols 1, 2512-6.

Lin H S, Hu C Y, Chan H Y, Liew Y Y, Huang H P, Lepescheux L, Bastianelli E, Baron R, Rawadi G, Clément-Lacroix P. (2007) Anti-rheumatic activities of histone deacetylase (HDAC) inhibitors in vivo in collagen-induced arthritis in rodents. Br J Pharmacol. April; 150 (7):829-31.

McGinnity et al. Drug Metabolism and Disposition 2008, 32, 11, 1247.

All publications, including but not limited to patents and patent applications, cited in this specification are herein incorporated by reference as if each individual publication were specifically and individually indicated to be incorporated by reference herein as though fully set forth.

From the foregoing description, various modifications and changes in the compositions and methods of this invention will occur to those skilled in the art. All such modifications coming within the scope of the appended claims are intended to be included therein.

It should be understood that factors such as the differential cell penetration capacity of the various compounds can contribute to discrepancies between the activity of the compounds in the in vitro biochemical and cellular assays.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using either ChemDraw® or ISIS® /DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

What is claimed is:

1. A compound according to Formula I:

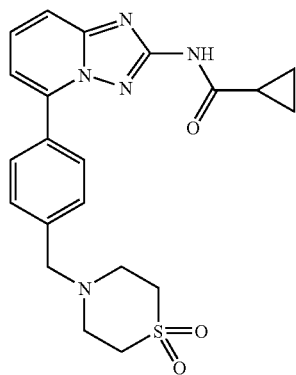

(I)

or a pharmaceutically acceptable salt thereof.

2. A pharmaceutical composition comprising a pharmaceutically acceptable carrier and a pharmaceutically effective amount of a compound according claim 1.

3. The pharmaceutical composition according to claim 2 comprising a further therapeutic agent selected from arthritis treatment agents.

4. The pharmaceutical composition according to claim 3, wherein the further therapeutic agent is an agent selected from analgesics, NSAIDS (non-steroidal anti-inflammatory drugs), and DMARDS (disease-modifying anti-rheumatic drugs).

5. A method for the treatment of rheumatoid arthritis, comprising administering an amount of a compound of claim 1, sufficient to effect said treatment.

6. The method according to claim 5, wherein the compound according to claim 1 is administered in combination with one or more further therapeutic agents selected from arthritis treatment agents.

7. The method according to claim 5, wherein the compound according to claim 1 is administered in combination with one further therapeutic agent selected from arthritis treatment agents.

8. A method for the treatment of rheumatoid arthritis, comprising administering an amount of a pharmaceutical composition of claim 2, sufficient to effect said treatment.

9. A method for the treatment of rheumatoid arthritis, comprising administering an amount of a pharmaceutical composition of claim 2, sufficient to effect said treatment.

10. The method according to claim 3, wherein said pharmaceutical composition is administered in combination with a further therapeutic agent selected from arthritis treatment agents.

11. The method according to claim 9, wherein said pharmaceutical composition is administered in combination with a further therapeutic agent selected from arthritis treatment agents.

12. The method according to claim 6, wherein the further therapeutic agent is an agent selected from analgesics, NSAIDS (non-steroidal anti-inflammatory drugs), and DMARDS (disease-modifying anti-rheumatic drugs).

13. The method according to claim 7, wherein the further therapeutic agent is an agent selected from analgesics, NSAIDS (non-steroidal anti-inflammatory drugs), and DMARDS (disease-modifying anti-rheumatic drugs).

14. The method according to claim 10, wherein the further therapeutic agent is an agent selected from analgesics, NSAIDS (non-steroidal anti-inflammatory drugs), and DMARDS (disease-modifying anti-rheumatic drugs).

15. The method according to claim 11, wherein the further therapeutic agent is an agent selected from analgesics, NSAIDS (non-steroidal anti-inflammatory drugs), and DMARDS (disease-modifying anti-rheumatic drugs).

* * * * *

UNITED STATES PATENT AND TRADEMARK OFFICE
CERTIFICATE OF CORRECTION

PATENT NO. : 8,088,764 B2
APPLICATION NO. : 12/823654
DATED : January 3, 2012
INVENTOR(S) : Christel Jeanne Marie Menet and Koen Kurt Smits It is certified that error appears in the above-identified patent and that said Letters Patent is hereby corrected as shown below:

In the Claims:

Column 60, lines 23-25, claim 9 should read:

9. A method for the treatment of rheumatoid arthritis, comprising administering an amount of a pharmaceutical composition of claim 3, sufficient to effect said treatment.

Column 60, lines 26-29, claim 10 should read:

10. The method according to claim 8, wherein said pharmaceutical composition is administered in combination with a further therapeutic agent selected from arthritis treatment agents.

Signed and Sealed this
Thirteenth Day of May, 2014

Michelle K. Lee
*Deputy Director of the United States Patent and Trademark Office*